(12) United States Patent
Walters et al.

(10) Patent No.: US 10,154,835 B2
(45) Date of Patent: Dec. 18, 2018

(54) VASCULAR CLOSURE DEVICE WITH CONFORMING PLUG MEMBER

(71) Applicant: ESSENTIAL MEDICAL, INC., Malvern, PA (US)

(72) Inventors: Greg Walters, Exton, PA (US); Todd Sorzano, Alpharetta, GA (US); Hunter Valentine, Malvern, PA (US)

(73) Assignee: Essential Medical, Inc., Exton, PA (US)

( * ) Notice: Subject to any disclaimer, the term of this patent is extended or adjusted under 35 U.S.C. 154(b) by 778 days.

(21) Appl. No.: 14/274,466

(22) Filed: May 9, 2014

(65) Prior Publication Data
US 2014/0336672 A1 Nov. 13, 2014

Related U.S. Application Data

(60) Provisional application No. 61/821,478, filed on May 9, 2013.

(51) Int. Cl.
*A61B 17/04* (2006.01)
*A61B 17/00* (2006.01)

(52) U.S. Cl.
CPC ............ *A61B 17/0057* (2013.01); *A61B 2017/00597* (2013.01); *A61B 2017/00619* (2013.01);
(Continued)

(58) Field of Classification Search
CPC ............ A61B 17/0401; A61B 17/0487; A61B 17/12109; A61B 17/12159;
(Continued)

(56) References Cited

U.S. PATENT DOCUMENTS 3,125,095 A 3/1964 Kaufman et al.
4,665,918 A 5/1987 Garza et al.
(Continued)

FOREIGN PATENT DOCUMENTS

EP 0474752 6/1995
EP 0766947 4/1997
(Continued)

OTHER PUBLICATIONS

U.S. Appl. No. 61/920,207, filed Dec. 23, 2013, Walters et al.
International Patent Application No. PCT/US/2012/061855; International Search Report dated Jan. 22, 2013, 21 pages.

*Primary Examiner* — Elizabeth Houston
*Assistant Examiner* — Mohamed Gabr
(74) *Attorney, Agent, or Firm* — Offit Kurman, P.A.; Gregory A. Grissett

(57) ABSTRACT

A vascular closure device includes a delivery assembly, an anchor member carried by the delivery assembly, and a suture attached to the anchoring member. A plug member can be disposed in the delivery assembly and attached to suture such that the plug member. The plug member includes a plug body, a pair of ridges that project from the plug body, and a select location disposed between the pair of ridges. The plug member configured to, in response to a force applied to the select location, transition from an insertion configuration, whereby the plug member is elongate along an insertion direction, into a collapsed configuration, whereby the plug member is collapsed along the insertion direction.

9 Claims, 13 Drawing Sheets

(52) U.S. Cl.
CPC ........... *A61B 2017/00623* (2013.01); *A61B 2017/00628* (2013.01); *A61B 2017/00637* (2013.01); *A61B 2017/00659* (2013.01); *A61B 2017/00663* (2013.01); *A61B 2017/0474* (2013.01); *A61B 2017/0475* (2013.01); *A61B 2017/0496* (2013.01)

(58) Field of Classification Search
CPC ........... A61B 2017/00659; A61B 2017/00637; A61B 2017/0004; A61B 2017/00663; A61B 2017/00672; A61B 2017/00898; A61B 2017/0498; A61B 2017/0406; A61B 2017/0458; A61B 2017/0464
See application file for complete search history.

(56) References Cited

U.S. PATENT DOCUMENTS

| | | |
|---|---|---|
| 4,744,364 A | 5/1988 | Kensey |
| 4,760,847 A | 8/1988 | Vaillancourt |
| 4,852,568 A | 8/1989 | Kensey |
| 4,852,586 A | 8/1989 | Haines |
| 4,890,612 A | 1/1990 | Kensey |
| 4,990,151 A | 2/1991 | Wallstén |
| 5,021,059 A | 6/1991 | Kensey et al. |
| 5,026,377 A | 6/1991 | Burton et al. |
| 5,061,274 A | 10/1991 | Kensey |
| 5,192,301 A * | 3/1993 | Kamiya ............ A61B 17/0057 604/907 |
| 5,192,302 A | 3/1993 | Kensey et al. |
| 5,222,974 A | 6/1993 | Kensey et al. |
| 5,258,015 A | 11/1993 | Li et al. |
| 5,269,809 A | 12/1993 | Hayhurst et al. |
| 5,282,827 A | 2/1994 | Kensey et al. |
| 5,292,309 A | 3/1994 | Van Tassel et al. |
| 5,304,187 A | 4/1994 | Green et al. |
| 5,306,254 A | 4/1994 | Nash et al. |
| 5,312,435 A | 5/1994 | Nash et al. |
| 5,324,306 A | 6/1994 | Makower et al. |
| 5,342,393 A | 8/1994 | Stack |
| 5,350,399 A | 9/1994 | Erlebacher et al. |
| 5,370,661 A | 12/1994 | Branch |
| 5,372,146 A | 12/1994 | Branch |
| 5,411,520 A | 5/1995 | Nash et al. |
| 5,441,517 A | 8/1995 | Kensey et al. |
| 5,478,353 A | 12/1995 | Yoon |
| 5,486,196 A | 1/1996 | Hirshowitz et al. |
| 5,531,759 A | 7/1996 | Kensey et al. |
| 5,545,178 A | 8/1996 | Kensey et al. |
| 5,549,633 A | 8/1996 | Evans et al. |
| 5,620,461 A | 4/1997 | Muijs Van De Moer et al. |
| 5,643,318 A | 7/1997 | Tsukernik et al. |
| 5,662,681 A | 9/1997 | Nash et al. |
| 5,676,689 A | 10/1997 | Kensey et al. |
| 5,681,334 A | 10/1997 | Evans et al. |
| 5,690,674 A | 11/1997 | Diaz |
| 5,700,277 A | 12/1997 | Nash et al. |
| 5,707,393 A | 1/1998 | Kensey et al. |
| 5,725,345 A | 3/1998 | Zhov |
| 5,725,551 A | 3/1998 | Myers et al. |
| 5,728,114 A | 3/1998 | Evans et al. |
| 5,759,193 A | 6/1998 | Burbank et al. |
| 5,810,884 A | 9/1998 | Kim |
| 5,861,004 A | 1/1999 | Kensey et al. |
| 5,916,236 A | 6/1999 | Muijs Van de Moer et al. |
| 5,935,147 A | 8/1999 | Kensey et al. |
| 6,007,563 A | 12/1999 | Nash et al. |
| 6,045,569 A | 4/2000 | Kensey et al. |
| 6,086,607 A | 7/2000 | Cragg et al. |
| 6,090,130 A | 7/2000 | Nash et al. |
| 6,120,524 A | 9/2000 | Taheri |
| 6,179,863 B1 | 1/2001 | Kensey et al. |
| 6,190,400 B1 | 2/2001 | Van De Moer et al. |
| 6,200,328 B1 | 3/2001 | Cragg et al. |
| 6,261,309 B1 | 7/2001 | Urbanski |
| 6,293,961 B2 | 9/2001 | Schwartz et al. |
| 6,306,159 B1 | 10/2001 | Schwartz et al. |
| 6,319,271 B1 | 11/2001 | Schwartz et al. |
| 6,329,564 B1 | 12/2001 | Lebner |
| 6,366,341 B1 | 4/2002 | Shirato et al. |
| 6,425,911 B1 | 7/2002 | Akerfeldt et al. |
| 6,432,123 B2 | 8/2002 | Schwartz et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,471,715 B1 | 10/2002 | Weiss |
| 6,494,848 B1 | 12/2002 | Sommercorn et al. |
| 6,508,828 B1 | 1/2003 | Akerfeldt et al. |
| 6,682,489 B2 | 1/2004 | Tenerz et al. |
| 6,712,837 B2 | 3/2004 | Åkerfeldt et al. |
| 6,764,500 B1 | 7/2004 | Muijs Van De Moer et al. |
| 6,786,915 B2 | 9/2004 | Akerfeldt et al. |
| 6,822,133 B2 | 11/2004 | Lebner |
| 6,831,205 B2 | 12/2004 | Lebner |
| 6,860,895 B1 | 3/2005 | Akerfeldt et al. |
| 6,929,655 B2 | 8/2005 | Egnelov et al. |
| 6,932,824 B1 | 8/2005 | Roop et al. |
| 6,939,363 B2 | 9/2005 | Åkerfeldt |
| 7,025,776 B1 | 4/2006 | Houser et al. |
| 7,044,916 B2 | 5/2006 | Tenerz et al. |
| 7,066,944 B2 | 6/2006 | Laufer et al. |
| 7,073,509 B2 | 7/2006 | Tenerz et al. |
| 7,101,381 B2 | 9/2006 | Ford et al. |
| 7,131,973 B2 | 11/2006 | Hoffman |
| 7,169,168 B2 | 1/2007 | Muijs Van De Moer et al. |
| 7,175,646 B2 | 2/2007 | Brenneman et al. |
| 7,250,057 B2 | 7/2007 | Forsberg |
| 7,285,097 B2 | 10/2007 | Tenerz et al. |
| 7,597,705 B2 | 10/2009 | Forsberg et al. |
| 7,618,436 B2 | 11/2009 | Forsberg |
| 7,618,438 B2 | 11/2009 | White et al. |
| 7,621,937 B2 | 11/2009 | Pipenhagen et al. |
| 7,641,694 B1 | 1/2010 | Goble et al. |
| 7,648,493 B2 | 1/2010 | Forsberg et al. |
| 7,678,135 B2 | 3/2010 | Maahs et al. |
| 7,691,127 B2 | 4/2010 | Yassinzadeh |
| 7,695,493 B2 | 4/2010 | Saadat et al. |
| 7,713,283 B2 | 5/2010 | Forsberg |
| 7,731,732 B2 | 6/2010 | Ken |
| 7,736,376 B2 | 6/2010 | Sato et al. |
| 7,736,379 B2 | 6/2010 | Ewers et al. |
| 7,749,247 B2 | 7/2010 | Tegg |
| 7,749,248 B2 | 7/2010 | White et al. |
| 7,749,250 B2 | 7/2010 | Stone et al. |
| 7,771,455 B2 | 8/2010 | Ken |
| 7,785,334 B2 | 8/2010 | Ford et al. |
| 7,806,905 B2 | 10/2010 | Ford et al. |
| 7,850,654 B2 | 12/2010 | Belhe et al. |
| 7,905,902 B2 | 3/2011 | Huitema et al. |
| 8,273,094 B2 | 9/2012 | Belhe et al. |
| 8,337,522 B2 | 12/2012 | Ditter |
| 8,382,793 B2 | 2/2013 | Egnelöv et al. |
| 8,540,750 B2 | 9/2013 | Tegels |
| 8,591,542 B2 | 11/2013 | White et al. |
| 8,974,476 B2 | 3/2015 | Tegels |
| 2001/0003158 A1 | 6/2001 | Kensey et al. |
| 2001/0044639 A1 | 11/2001 | Levinson |
| 2001/0051815 A1 | 12/2001 | Esplin |
| 2003/0060846 A1 | 3/2003 | Egnelov et al. |
| 2003/0078616 A1 | 4/2003 | Ginn et al. |
| 2003/0088271 A1 | 5/2003 | Cragg et al. |
| 2003/0233120 A1 | 12/2003 | Akerfeldt |
| 2004/0093025 A1 | 5/2004 | Egnelov |
| 2004/0098046 A1 | 5/2004 | Tenerz et al. |
| 2004/0138674 A1 | 7/2004 | Egnelov et al. |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0225305 A1 | 11/2004 | Ewers et al. |
| 2004/0243007 A1 | 12/2004 | Tenerz et al. |
| 2004/0267308 A1 | 12/2004 | Bagaoisan et al. |
| 2005/0049634 A1 | 3/2005 | Chopra |
| 2005/0080452 A1 | 4/2005 | Akerfeldt |
| 2005/0085851 A1 | 4/2005 | Fiehler et al. |

(56) References Cited

U.S. PATENT DOCUMENTS

| | | |
|---|---|---|
| 2005/0085852 A1 | 4/2005 | Ditter |
| 2005/0085855 A1 | 4/2005 | Forsberg |
| 2005/0090860 A1 | 4/2005 | Paprocki |
| 2005/0096696 A1 | 5/2005 | Forsberg |
| 2005/0096697 A1 | 5/2005 | Forsberg et al. |
| 2005/0107820 A1 | 5/2005 | Forsberg et al. |
| 2005/0107827 A1 | 5/2005 | Paprocki |
| 2005/0121042 A1 | 6/2005 | Belhe et al. |
| 2005/0125030 A1 | 6/2005 | Forsberg et al. |
| 2005/0125031 A1* | 6/2005 | Pipenhagen ....... A61B 17/0057 606/213 |
| 2005/0131459 A1 | 6/2005 | Akerfeldt |
| 2005/0137624 A1 | 6/2005 | Fallman |
| 2005/0149069 A1 | 7/2005 | Bertolero et al. |
| 2005/0161459 A1 | 7/2005 | Shelstad |
| 2005/0166974 A1 | 8/2005 | Hashiguchi |
| 2005/0169974 A1 | 8/2005 | Tenerz et al. |
| 2005/0204035 A1 | 9/2005 | Kalish |
| 2005/0234396 A1 | 10/2005 | Forsberg et al. |
| 2005/0251210 A1 | 11/2005 | Westra et al. |
| 2005/0267521 A1 | 12/2005 | Forsberg |
| 2005/0277981 A1 | 12/2005 | Maahs et al. |
| 2005/0283193 A1 | 12/2005 | Tullberg et al. |
| 2006/0004408 A1 | 1/2006 | Morris et al. |
| 2006/0058844 A1 | 3/2006 | White et al. |
| 2006/0142797 A1 | 6/2006 | Egnelov |
| 2006/0173492 A1 | 8/2006 | Akerfeldt et al. |
| 2006/0206146 A1 | 9/2006 | Tenerz |
| 2006/0229672 A1 | 10/2006 | Forsberg |
| 2006/0229673 A1 | 10/2006 | Forsberg |
| 2006/0229674 A1 | 10/2006 | Forsberg |
| 2006/0229675 A1 | 10/2006 | Novoa et al. |
| 2006/0265006 A1 | 11/2006 | White et al. |
| 2006/0265007 A1 | 11/2006 | White et al. |
| 2007/0032823 A1 | 2/2007 | Tegg |
| 2007/0032824 A1 | 2/2007 | Terwey |
| 2007/0073345 A1 | 3/2007 | Pipenhagen et al. |
| 2007/0123936 A1 | 5/2007 | Goldin et al. |
| 2007/0135842 A1 | 6/2007 | Van de Moer et al. |
| 2007/0150002 A1 | 6/2007 | Szabo et al. |
| 2007/0156084 A1 | 7/2007 | Belhe et al. |
| 2007/0156245 A1 | 7/2007 | Cauthen et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0255314 A1 | 11/2007 | Forsberg |
| 2007/0276433 A1 | 11/2007 | Huss |
| 2007/0276435 A1 | 11/2007 | Yassinzadeh et al. |
| 2007/0282373 A1 | 12/2007 | Ashby et al. |
| 2008/0071311 A1 | 3/2008 | White et al. |
| 2008/0097509 A1 | 4/2008 | Beyar et al. |
| 2008/0097521 A1 | 4/2008 | Khosravi et al. |
| 2008/0097522 A1 | 4/2008 | Chopra |
| 2008/0114395 A1 | 5/2008 | Mathisen et al. |
| 2008/0221616 A1 | 9/2008 | Ginn et al. |
| 2009/0024161 A1 | 1/2009 | Bonutti et al. |
| 2009/0030450 A1 | 1/2009 | Preinitz et al. |
| 2009/0036919 A1 | 2/2009 | Preinitz et al. |
| 2009/0036920 A1 | 2/2009 | Preinitz et al. |
| 2009/0043333 A1 | 2/2009 | Preinitz et al. |
| 2009/0054926 A1 | 2/2009 | Pipenhagen et al. |
| 2009/0062850 A1 | 3/2009 | Ken |
| 2009/0069844 A1 | 3/2009 | Green et al. |
| 2009/0112257 A1 | 4/2009 | Preinitz et al. |
| 2009/0143817 A1 | 6/2009 | Akerfeldt |
| 2009/0171281 A1 | 7/2009 | Pipenhagen et al. |
| 2009/0171387 A1 | 7/2009 | Pipenhagen et al. |
| 2009/0216267 A1 | 8/2009 | Willard et al. |
| 2009/0234377 A1 | 9/2009 | Mahlin et al. |
| 2009/0248064 A1 | 10/2009 | Preinitz |
| 2009/0254110 A1 | 10/2009 | Bagaoisan et al. |
| 2009/0270885 A1 | 10/2009 | Maruyama et al. |
| 2009/0270911 A1 | 10/2009 | Shipp |
| 2009/0312790 A1 | 12/2009 | Forsberg et al. |
| 2010/0023051 A1 | 1/2010 | White et al. |
| 2010/0042144 A1 | 2/2010 | Bennett |
| 2010/0049245 A1 | 2/2010 | Cragg et al. |
| 2010/0145366 A1 | 6/2010 | Roop et al. |
| 2010/0145383 A1 | 6/2010 | Yassinzadeh |
| 2010/0145385 A1 | 6/2010 | Surti et al. |
| 2010/0168789 A1 | 7/2010 | Bagaoisan et al. |
| 2010/0174312 A1 | 7/2010 | Maahs et al. |
| 2010/0179588 A1 | 7/2010 | Sater et al. |
| 2010/0179589 A1 | 7/2010 | Roorda et al. |
| 2010/0185234 A1 | 7/2010 | Fortson et al. |
| 2010/0191280 A1 | 7/2010 | Forsberg |
| 2010/0211000 A1 | 8/2010 | Killion et al. |
| 2010/0217308 A1 | 8/2010 | Hansen |
| 2010/0217309 A1 | 8/2010 | Hansen et al. |
| 2010/0217310 A1 | 8/2010 | Shoemaker et al. |
| 2010/0217311 A1 | 8/2010 | Jenson et al. |
| 2010/0217312 A1 | 8/2010 | Hill et al. |
| 2010/0222796 A1 | 9/2010 | Brett et al. |
| 2010/0234883 A1 | 9/2010 | White et al. |
| 2010/0256673 A1 | 10/2010 | Coleman et al. |
| 2010/0275432 A1 | 11/2010 | Pikus et al. |
| 2010/0286727 A1 | 11/2010 | Terwey |
| 2011/0009853 A1 | 1/2011 | Bertolero et al. |
| 2011/0046663 A1 | 2/2011 | Zhou et al. |
| 2011/0046665 A1 | 2/2011 | Green et al. |
| 2011/0054456 A1 | 3/2011 | Thompson et al. |
| 2011/0066181 A1 | 3/2011 | Jenson et al. |
| 2011/0077598 A1 | 3/2011 | Pipenhagen et al. |
| 2011/0077683 A1 | 3/2011 | Huss |
| 2011/0172702 A1 | 7/2011 | Fiehler et al. |
| 2011/0178548 A1 | 7/2011 | Tenerz |
| 2011/0196388 A1 | 8/2011 | Thielen et al. |
| 2011/0213410 A1 | 9/2011 | Ginn et al. |
| 2011/0213411 A1 | 9/2011 | Ginn et al. |
| 2011/0213412 A1 | 9/2011 | Ginn et al. |
| 2011/0213449 A1 | 9/2011 | Ginn et al. |
| 2011/0224728 A1 | 9/2011 | Martin et al. |
| 2011/0270302 A1 | 11/2011 | Forsberg |
| 2011/0288580 A1 | 11/2011 | Ginn et al. |
| 2011/0295316 A1 | 12/2011 | Ginn et al. |
| 2011/0301619 A1 | 12/2011 | Walters |
| 2011/0301638 A1* | 12/2011 | Walters ............... A61B 17/0057 606/213 |
| 2012/0010634 A1 | 1/2012 | Crabb et al. |
| 2012/0022585 A1 | 1/2012 | Atanasoska et al. |
| 2012/0065668 A1 | 3/2012 | Ginn et al. |
| 2012/0071919 A1 | 3/2012 | Pipenhagen et al. |
| 2012/0083829 A1 | 4/2012 | Ginn et al. |
| 2012/0109192 A1 | 5/2012 | Egnelov et al. |
| 2012/0116446 A1 | 5/2012 | Green et al. |
| 2012/0143245 A1 | 6/2012 | Tegels |
| 2012/0158044 A1 | 6/2012 | Jenson et al. |
| 2012/0245517 A1 | 9/2012 | Tegels |
| 2012/0245597 A1 | 9/2012 | Tegels |
| 2012/0245624 A1 | 9/2012 | Glazier et al. |
| 2012/0283770 A1 | 11/2012 | Kramer et al. |
| 2012/0296275 A1 | 11/2012 | Martin et al. |
| 2013/0006298 A1 | 1/2013 | Terwey |
| 2013/0035719 A1 | 2/2013 | Hill et al. |
| 2013/0072949 A1 | 3/2013 | Halac et al. |
| 2013/0079802 A1 | 3/2013 | Halac et al. |
| 2013/0103077 A1 | 4/2013 | Ditter |
| 2013/0144316 A1 | 6/2013 | McCrea et al. |
| 2013/0150884 A1 | 6/2013 | Belhe et al. |
| 2013/0178895 A1 | 7/2013 | Walters et al. |
| 2014/0046217 A1 | 2/2014 | Lim |
| 2014/0046220 A1 | 2/2014 | Nelson |
| 2014/0094846 A1 | 4/2014 | Lim |
| 2014/0188160 A1 | 7/2014 | Tegels |
| 2015/0068009 A1 | 3/2015 | Walters |
| 2015/0100083 A1 | 4/2015 | Walters et al. |

FOREIGN PATENT DOCUMENTS

| | | |
|---|---|---|
| EP | 0797953 | 10/1997 |
| EP | 1169968 | 1/2002 |
| EP | 1222896 | 7/2002 |
| EP | 1254634 | 11/2002 |

(56) References Cited

FOREIGN PATENT DOCUMENTS

| | | |
|---|---|---|
| EP | 0664687 | 8/2003 |
| EP | 1371333 | 12/2003 |
| EP | 1413255 | 4/2004 |
| EP | 1440661 | 7/2004 |
| EP | 1532929 | 5/2005 |
| EP | 165881 | 5/2006 |
| EP | 1695667 | 8/2006 |
| EP | 1836967 | 9/2007 |
| EP | 1836968 | 9/2007 |
| EP | 2055236 | 5/2009 |
| EP | 2064999 | 6/2009 |
| EP | 2213247 | 8/2010 |
| EP | 2215974 | 8/2010 |
| EP | 1919367 | 10/2011 |
| EP | 1874195 | 1/2012 |
| EP | 1893100 | 3/2012 |
| EP | 2227148 | 4/2012 |
| EP | 1893099 | 6/2012 |
| EP | 1893098 | 1/2014 |
| EP | 2611366 | 7/2014 |
| EP | 2605707 | 10/2014 |
| WO | WO 1989/11301 | 11/1989 |
| WO | WO 1990/14796 | 12/1990 |
| WO | WO 1993/08743 | 5/1993 |
| WO | WO 1993/08746 | 5/1993 |
| WO | WO 1994/07421 | 4/1994 |
| WO | WO 1998/05259 | 2/1998 |
| WO | WO 1999/22646 | 5/1999 |
| WO | WO 2000/078226 | 12/2000 |
| WO | WO 2003/094740 | 11/2003 |
| WO | WO 2004/096056 | 11/2004 |
| WO | WO 2005/002451 | 1/2005 |
| WO | WO 2005/039387 | 5/2005 |
| WO | WO 2005/060514 | 7/2005 |
| WO | WO 2006/075228 | 7/2006 |
| WO | WO 2006/110615 | 10/2006 |
| WO | WO 2007/035187 | 3/2007 |
| WO | WO 2008/036634 | 3/2008 |
| WO | WO 2009/005722 | 1/2009 |
| WO | WO 2009/025836 | 2/2009 |
| WO | WO 2009/035921 | 3/2009 |
| WO | WO 2009/088440 | 7/2009 |
| WO | WO 2009/088441 | 7/2009 |
| WO | WO 2009/112930 | 9/2009 |
| WO | WO 2010/0129042 | 11/2010 |
| WO | WO 2011/014244 | 2/2011 |
| WO | WO 2011/019374 | 2/2011 |
| WO | WO 2011/025529 | 3/2011 |
| WO | WO 2011/025543 | 3/2011 |
| WO | WO 2011/037635 | 3/2011 |
| WO | WO 2011/146729 | 11/2011 |
| WO | WO 2011/156498 | 12/2011 |
| WO | WO 2012/009007 | 1/2012 |
| WO | WO 2012/012641 | 1/2012 |
| WO | WO 2012/045356 | 4/2012 |
| WO | WO 2012/061486 | 5/2012 |
| WO | WO 2012/064888 | 5/2012 |
| WO | WO 2012/083045 | 6/2012 |
| WO | WO 2012/145356 | 10/2012 |
| WO | WO 2012/145362 | 10/2012 |
| WO | WO 2012/148745 | 11/2012 |
| WO | WO 2012/148747 | 11/2012 |
| WO | WO 2012/158662 | 11/2012 |
| WO | WO 2012/158737 | 11/2012 |
| WO | WO 2012/158738 | 11/2012 |
| WO | WO 2012/158740 | 11/2012 |
| WO | WO 2012/158931 | 11/2012 |
| WO | WO 2013/063227 A1 | 5/2013 |
| WO | WO 2013/081659 | 6/2013 |

* cited by examiner

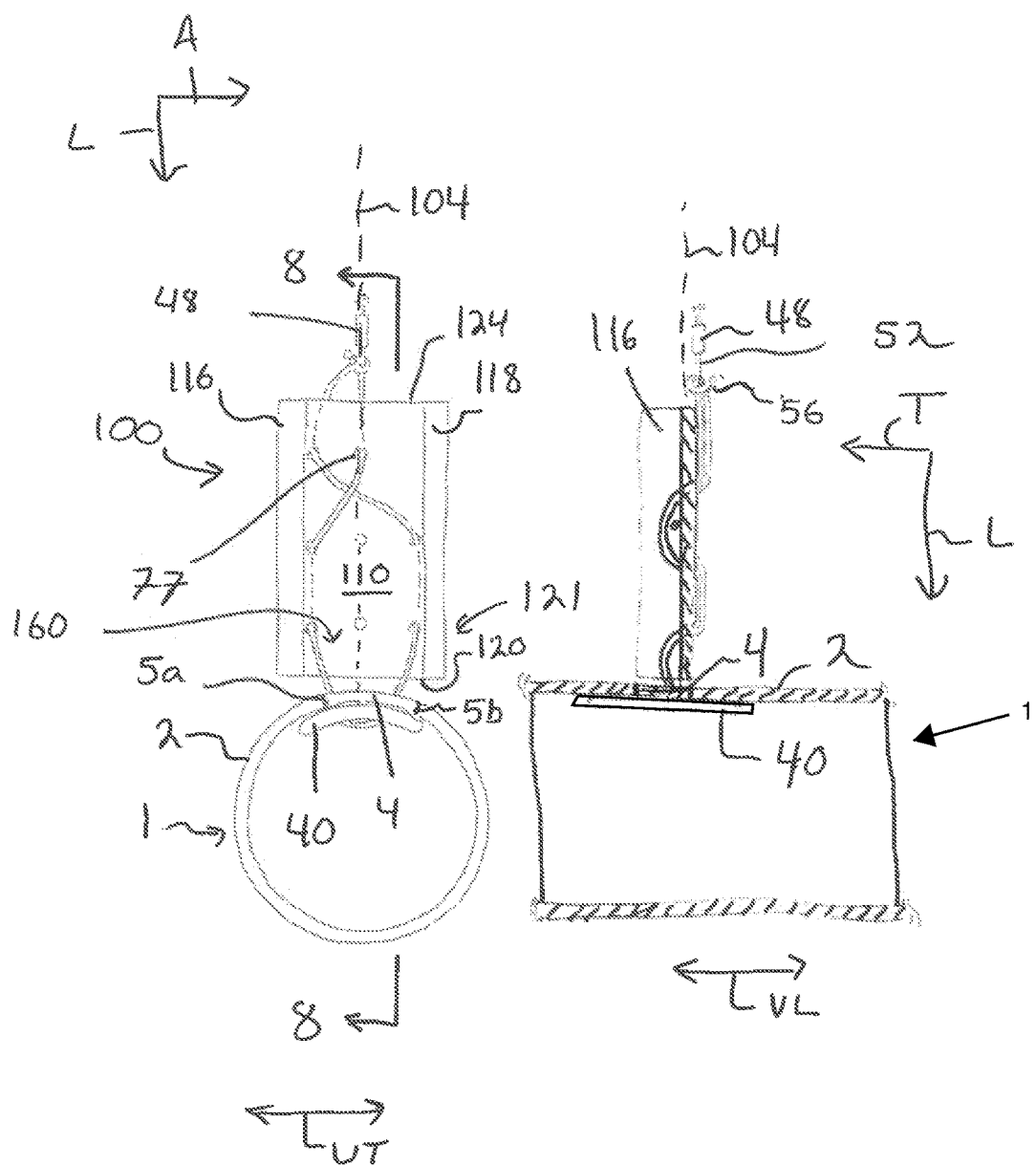

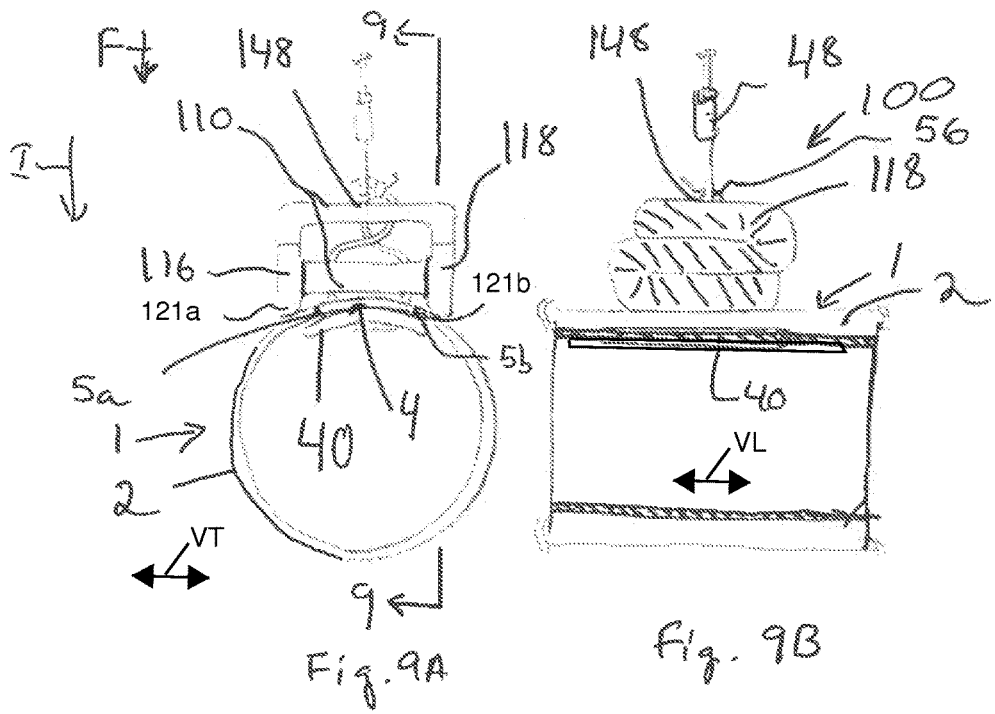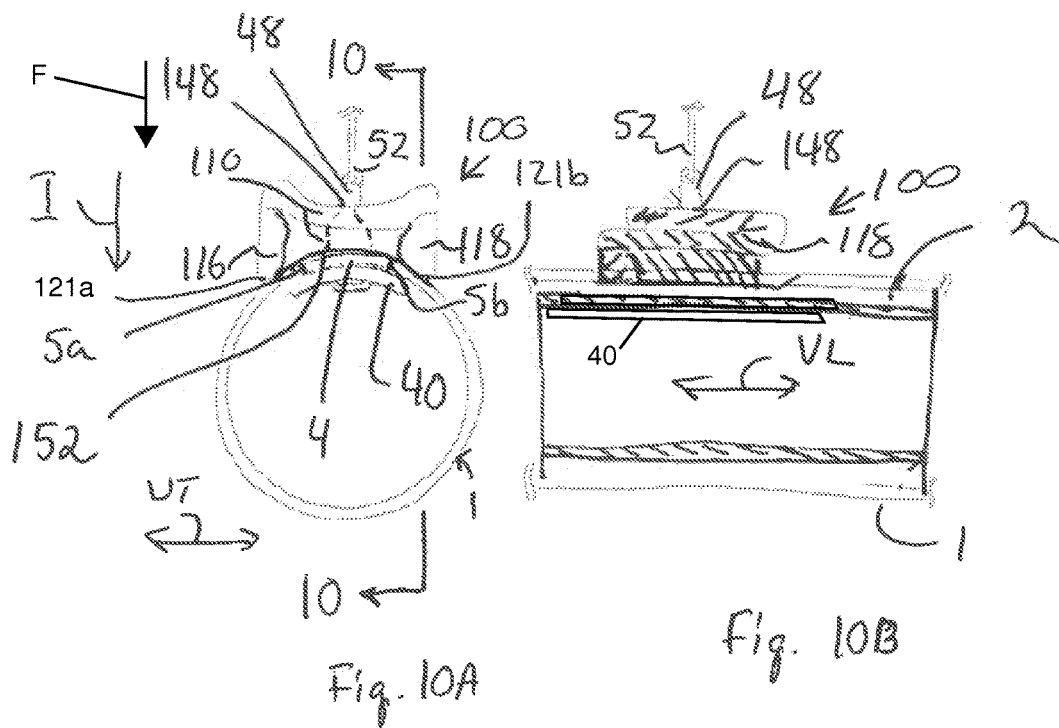

VASCULAR CLOSURE DEVICE WITH CONFORMING PLUG MEMBER

CROSS REFERENCE TO RELATED APPLICATIONS

This application claims the benefit of U.S. Provisional Patent Application Ser. No. 61/821,478 filed May 9, 2013, the entire disclosure of which is hereby incorporated by reference as if set forth in its entirety herein.

FIELD OF THE INVENTION

The present disclosure relates to a vascular closure, and in particular, to a vascular closure device that includes a plug member configured to cover a puncture in a vessel and conform around the vessel.

BACKGROUND

Percutaneous access of the vascular system for vascular device delivery is a common medical procedure. Typically, this involves using a hollow needle to puncture a vessel, then introducing an introducer sheath to open the puncture for the introduction of catheters and wire guides for navigation through the vascular system to facilitate delivery. For example, in many cases, vascular access requires introduction of catheters and wire guides through the femoral artery. Once the procedure is completed, the devices are removed from the patient and pressure is applied to the puncture to stop the bleeding. Thereafter, the puncture may be sealed using a closure device. As the size of percutaneous sheaths become larger to accommodate larger vascular devices, the size of the resulting puncture increases. Larger punctures are harder to seal with typical vascular closure devices.

SUMMARY

An embodiment of the present disclosure is a vascular closure device. The vascular closure device includes a delivery assembly configured to be inserted into a puncture of a vessel, an anchor member carried by the delivery assembly, and a suture attached to the anchoring member and extending into the delivery assembly. The vascular closure device includes a plug member disposed in the delivery assembly and attached to suture such that the plug member is proximal to the anchor member. The plug member includes a plug body, a pair of ridges that project from the plug body, and a select location disposed between the pair of ridges. The plug member configured to, in response to a force applied to the select location, transition from an insertion configuration, whereby the plug member is elongate along an insertion direction, into a collapsed configuration, whereby the plug member is collapsed along the insertion direction. When the plug member is deployed against the puncture in the collapsed configuration, a portion of the plug body and a portion of the pair of ridges cover the puncture and conforms to the shape of the vessel adjacent the puncture.

Another embodiment of the present disclosure is a vascular closure device having a plug member. The plug member is elongate along a first axis and further includes a plug body, a first ridge, and a second ridge spaced from the first ridge along a second axis that intersects and is angularly offset with respect to the first axis. The first and second ridges each project from the plug body. The plug member is configured to, in response to a force applied the plug body between the first and ridges, transition from an insertion configuration, whereby the plug member is elongate along an insertion direction, into a collapsed configuration, whereby the plug member is collapsed along the insertion direction. When the plug member is in the collapsed configuration, a portion of the first and second ridges and a portion of the plug body at least partially define a vessel engaging portion that conforms to a shape of the of a vessel along the puncture.

Another embodiment of the present disclosure includes a method for sealing a puncture in a vessel. The method includes the step of advancing a closure device toward the puncture along an insertion direction. The closure device includes an anchor member, a suture attached to the anchor member, and a plug member carried by the suture and being moveable along the suture toward the anchor member in the insertion direction. The plug member includes at least one pair of ridges that are spaced apart along a direction that is angularly offset with respect to the insertion direction. The method can include positioning the anchor member relative to an inner surface of vessel at the puncture. Further, the method can include causing the plug member to collapse along the insertion direction against the vessel opposite the anchor member, such that, a portion of the at least one pair of ridges and the plug body covers the puncture and conforms to a shape of the vessel.

BRIEF DESCRIPTION OF THE DRAWINGS

The foregoing summary, as well as the following detailed description of an exemplary embodiments of the present disclosure, will be better understood when read in conjunction with the appended drawings, in which there is shown in the drawings example embodiments for the purposes of illustration. It should be understood, however, that the application is not limited to the precise arrangements and systems shown. In the drawings:

FIG. 8A is a schematic end view of a portion of the sealing device shown in FIG. 1, showing an anchor member inside the vessel and the plug member in an insertion configuration;

FIG. 8B is a cross-sectional view of the sealing device and the vessel taken along lines 8B-8B in FIG. 8A;

FIG. 9A is a schematic an end view of a portion of the sealing device in FIG. 1, showing the plug member in an intermediate configuration partially collapsed on the vessel;

FIG. 9B is a cross-sectional view of the sealing device and the vessel taken along lines 9B-9B in FIG. 9A;

FIG. 10A is a schematic end view of a portion of the sealing device shown in FIG. 1, showing the toggle inside the vessel and the plug member locked in a collapsed configuration over a puncture;

FIG. 10B is a cross-sectional view of the sealing device and the vessel taken along lines 10B-10B in FIG. 10A;

DETAILED DESCRIPTION OF ILLUSTRATIVE EMBODIMENTS

Figure 1:
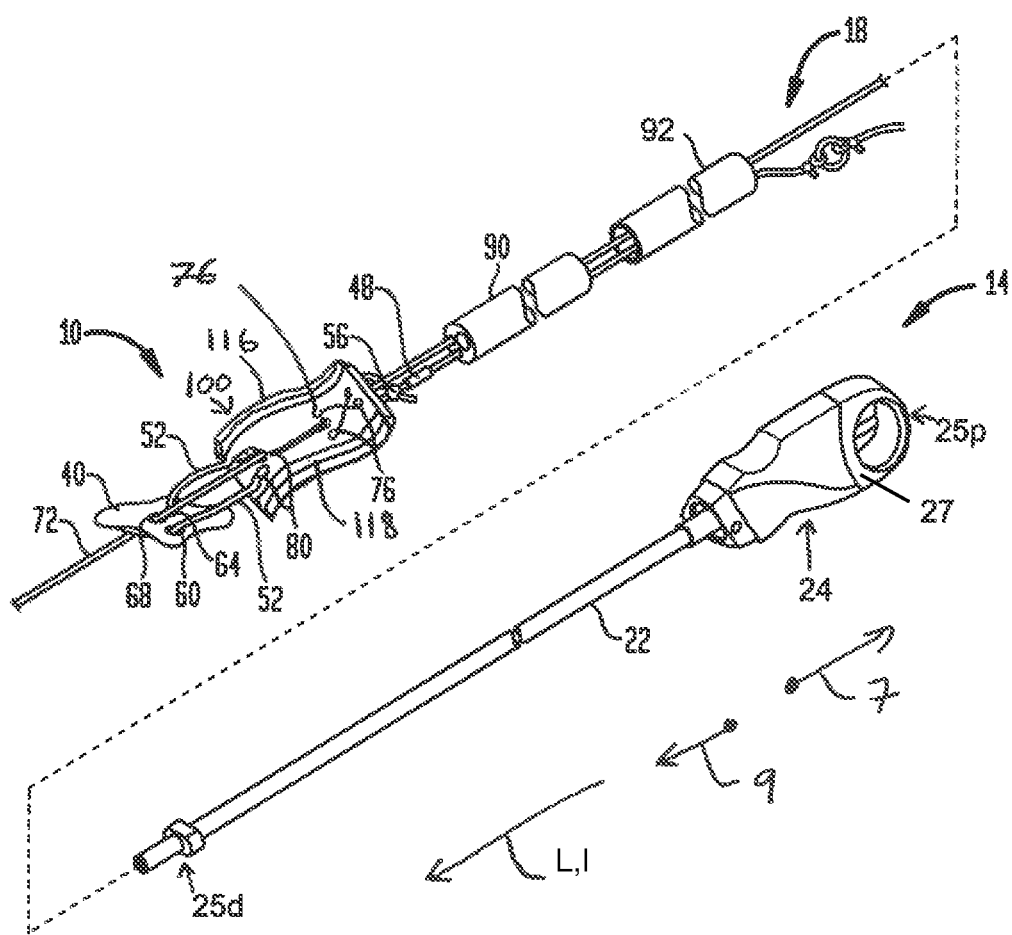
FIG. 1 is a perspective view of a puncture sealing device having a deployment assembly and a closure device disposed within the deployment assembly, according to an embodiment of the present disclosure.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Figure 2:
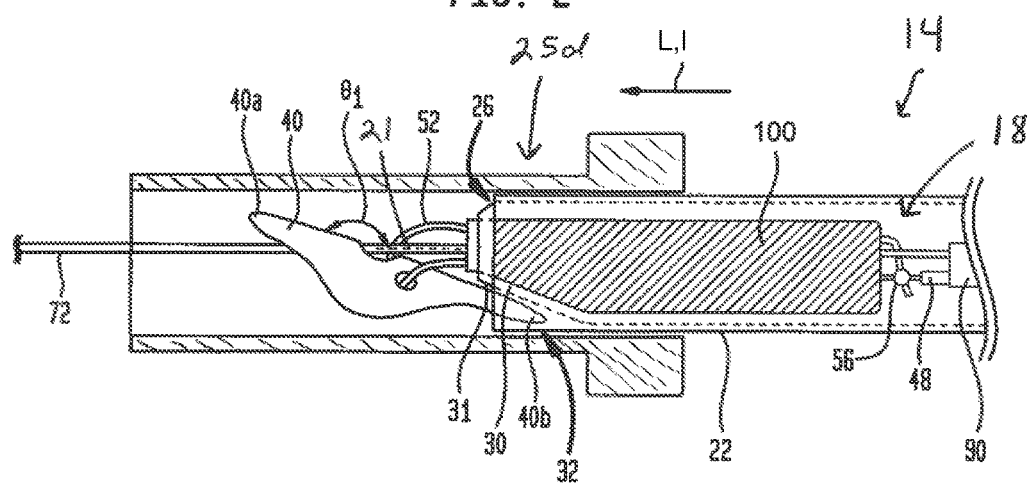
FIG. 2 is a detailed partial sectional view of a portion of the puncture sealing device shown in FIG. 1.
Figure 4:
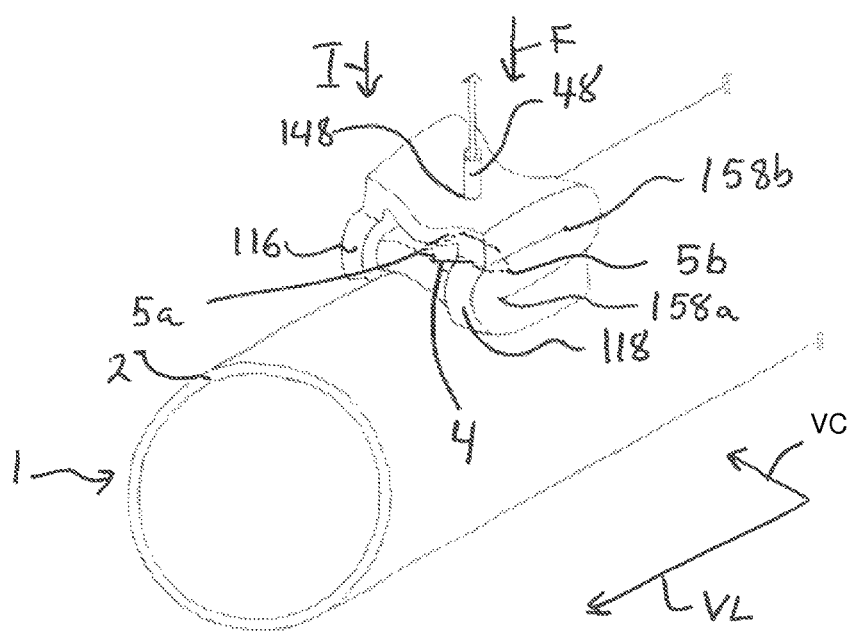
FIG. 4 is a perspective view of a portion of the sealing device shown in FIG. 1, showing the plug member in an collapsed configuration and covering a puncture of a vessel.

Referring to FIGS. 1, 2 and 4, a puncture sealing device 10 in accordance with an embodiment of the present disclosure can include a deployment assembly 14 and a closure device 18 at least partially disposed within the deployment assembly 14. After the deployment assembly 14 is inserted into a vessel 1 through a puncture 4 of the vessel, the closure device 18 is deployed from the deployment assembly 14 and locked against the puncture 4 to thereby seal or otherwise close the puncture of the vessel 1. The closure device 18 can include a plug member 100 with first and second ridges 116 and 118 arranged on the plug member 100 so that the plug member 100 can partially surround a portion of the vessel 1 and properly cover the puncture when the closure device 18 is locked in place. When the closure device 18 is deployed such that the plug member 100 is locked in place, the first and second ridges 116 and 118 abut the vessel 1 at locations adjacent or spaced from opposed transverse ends of the puncture 4. Accordingly, when the closure device 18 is locked in place against the puncture, locking forces are distributed across the plug member 100 at least in a direction transverse to the length of the vessel 1 such that ridges 116 and 118 abut and are compressed against the surface of vessel 1, thereby sealing the puncture 4 and improving hemostasis.

Continuing with FIG. 1, the deployment assembly 14 is elongate along a longitudinal direction L and includes a proximal end 25p and a distal end 25d spaced from the proximal end 25p in the longitudinal direction L. The longitudinal direction L can include and define a proximal direction 7 that extends from distal end 25d of the closure device 18 toward the proximal end 25p the closure device 18. Further, the longitudinal direction L can include and define a distal direction 9 that is opposite to the proximal direction 7 and extends from the proximal end 25p toward the distal end 25d. The deployment assembly 14 is configured to insert at least a portion of the closure device 18 into the vessel along an insertion direction I (see FIG. 4). The longitudinal direction L can be aligned with the insertion direction I during a portion of the sealing procedure.

As shown in FIG. 1 the deployment assembly 14 includes a housing 24 and a release tube 22 that extends relative to the housing 24 in a longitudinal direction L. The release tube 22 is elongate along the longitudinal direction L and defines a release tube channel 26 that extends through the release tube 22 along the longitudinal direction L. The release tube 22 is configured to restrain an anchor member 40, for instance a toggle 40, of the closure device 18 during insertion of the sealing device 10 into the vessel and subsequently release the toggle 40 so that the toggle 40 can be oriented for the sealing procedure.

As shown in FIG. 2, the deployment assembly 14 further includes a delivery tube 30 that is disposed within the release tube channel 26. The deployment assembly 14 is configured such that at least one of the release tube 22 and the delivery tube 30 is movable relative to the other along the longitudinal direction L. Therefore, the release tube 22 and the delivery tube 30 can be configured such that at least one of the release tube 22 and the delivery tube 30 is movable relative to the other to thereby release the toggle 40 and subsequently orient the toggle 40 for the sealing procedure.

Referring to FIGS. 1 and 2, the deployment assembly 14 further includes actuator 27 supported by the housing 24. The actuator 27 is configured to be coupled to at least one of the release tube 22 and the delivery tube 30 (FIG. 2) (coupling between actuator 27 not shown). In accordance with the illustrated embodiment, the actuator 27 can be pulled in the proximal direction 7 so as to cause at least one of the release tube 22 and the delivery tube 30 to move relative to the other to thereby release the toggle 40 and subsequently orient the toggle 40 for the sealing procedure. It should be appreciated any type of actuator can be used to cause the movement of the release tube 22 and/or the delivery tube 30 relative to each other.

In an alternative embodiment, one or more actuators can be used to cause the release of the toggle 40 from the delivery tube 30 and tension of the suture 52. For instance, the deployment assembly 14 can include an actuator coupled to the release tube 22 and the housing 24. The release tube 22 can be operatively associated with a tensioning device 92 (FIG. 1) such that continuous movement of the actuator relative to the housing 24 will move the release tube 22 to thereby release the toggle 40 from the release tube 22 and subsequently apply tension to the suture 52. It should be appreciated, however, that in some embodiments the suture 52 can be tensioned as the toggle 40 is being released. Further, the deployment assembly 14 can include a first actuator to release the toggle 40 and a second actuator that applies tension to the suture 52. For instance, the one or more actuators can be configured similarly to the actuator as described in U.S. Provisional Application Ser. No. 61/920, 207, filed Dec. 23, 2013 and pending at the filing of the present application. The contents of U.S. Provisional Application Ser. No. 61/920,207 are incorporated by the reference in this disclosure as if set forth in its entirety herein.

As shown in FIG. 2, the delivery tube 30 includes an angled portion 31 at its distal end. The angled portion 31 angles toward a central axis of the delivery tube 30 such that a retention cavity 32 is defined between the angled portion 31 and the release tube 22. The retention cavity 32 is sized to receive and retain a portion of the toggle 40 to thereby trap the toggle 40 between the delivery tube 30 and the release tube 22 such that the toggle 40 is angled by a first angle $Ø_1$ relative to a central axis 21 of the release tube 22. While the toggle 40 is trapped, the closure device 18 and deployment assembly 14 can be inserted into the vessel.

The closure device 18 is at least partially disposed within the delivery tube 30 prior to being inserted into the vessel. As shown in FIGS. 1 and 2, the closure device 18 further includes the plug member 100, a locking member 48, and a suture 52 that couples the toggle 40, plug member 100, and locking member 48 together such that the toggle 40 is distal to the plug member 100 and the locking member 48 is proximal to the plug member 100. As shown in FIG. 1, the suture 52 extends through the locking member 48, plug member 100, and toggle 40 in the longitudinal direction L, for instance the distal direction 9, and then back through the toggle 40 and plug member 100 in the proximal direction 7. An end of the suture 52 is then formed into a slidable knot 56 that is slidable along the suture 52 between the plug member 100 and the locking member 48. The suture 52 can be any elongate member, such as, for example a filament, thread, or braid. In operation, the locking member 48 and toggle 40 squeeze the plug member 100 against the puncture 4 to sealing the puncture. A force F (see FIG. 4) can be applied to the plug member 100 in the longitudinal direction L, which compresses the plug member 100 against the vessel, as will be further detailed below.

Continuing with FIGS. 1 and 2, the toggle 40 can be an elongate member that is configured to be seated inside the vessel against the vessel wall contiguous with the puncture. The toggle 40 defines a distal end 40a that is distal to a distal end of the release tube 22 and a proximal end 40b that is trapped within the retention cavity 32 between the release tube 22 and the delivery tube 30 during insertion of the toggle 40 into the vessel. The toggle further defines a first suture receiving aperture 60 that receives the suture 52 as it passes through the toggle 40 along the longitudinal direction L, for instance in the distal direction 9, a second suture receiving aperture 64 that receives the suture 52 as it passes through the toggle 40 in the proximal direction 7, and a guide wire aperture 68 that is configured to receive a guide wire 72 such that the closure device 18 is translatable along the guide wire 72 and is guided toward the puncture by the guide wire 72. The toggle 40 can be made of any biocompatible material. For example, the toggle 40 can made of a polylactic-coglycolic acid or other synthetic absorbable polymer that degrades in the presence of water into naturally occurring metabolites. In other embodiments, the toggle can be made of stainless steel, biocorrodible iron, and biocorrodible magnesium. It should be appreciated, however, that the toggle 40 can be made of other materials and can have other configurations so long as it can be seated inside the vessel against the vessel wall.

Figure 3:
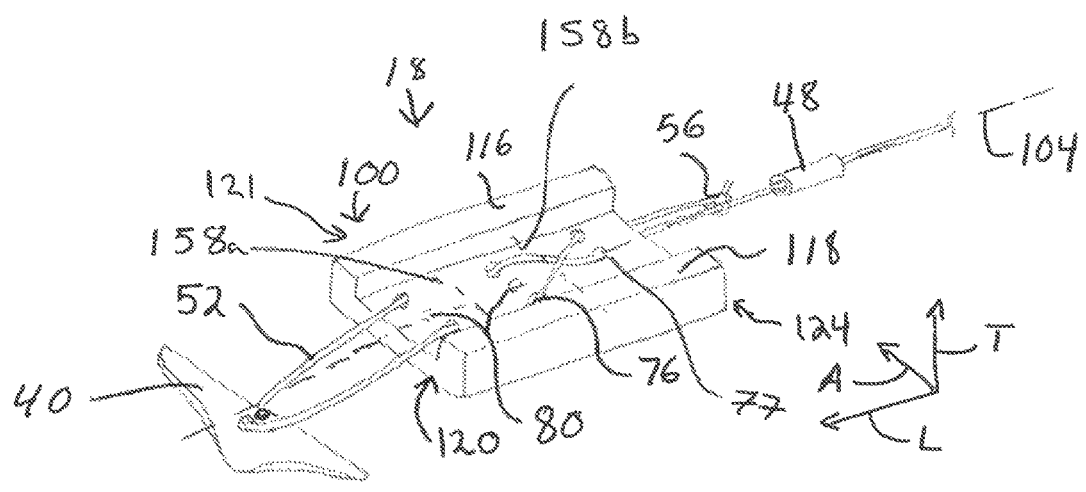
FIG. 3 is a perspective view of a portion of the sealing device shown in FIG. 1, showing a plug member of the closure device in an insertion configuration.

Turning to FIGS. 3 and 4, the plug member 100 is coupled to suture 52 between the toggle 40 and the locking member 48. The plug member 100 is moveable along the suture toward the toggle 40 along the longitudinal direction L for instance in the insertion direction I. The plug member 100 is configured to transition along the suture 52 from the insertion configuration shown in FIG. 3, whereby the plug member 100 is elongate along the longitudinal direction L, into the collapsed configuration shown in FIG. 4, whereby the plug member 100 is collapsed against the puncture 4 and conforms to the curvature of the vessel 1. When the plug member 100 is in the collapsed configuration against the vessel wall 2, a portion of the ridges 116 and 118 can be aligned with a longitudinal vessel direction VL such that the first and second ridges 116 and 118 contact the vessel wall 2 at spaced apart locations proximate to from opposed transverse ends 5a and 5b of the puncture 4. In accordance with the illustrated embodiment, the plug member 100 is configured to fold about one or more fold axes 158a and 158b as the plug member 100 collapses into the collapsed configuration along the insertion direction I. The plug member 100 can be configured to collapse via mechanisms other than folding.

Figure 5:
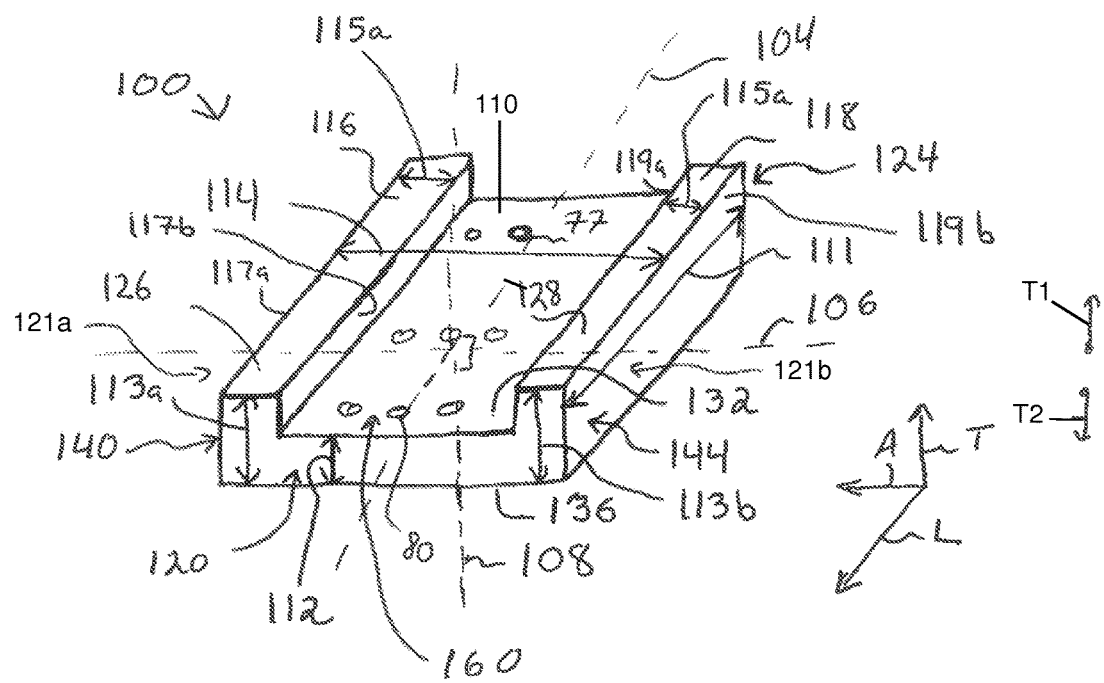
FIG. 5 is a perspective view of the plug member shown in FIG. 1.

Continuing with FIGS. 3-5, the plug member 100 includes a plug body 110 and the first and second ridges 116 and 118 project from the plug body 110. As noted above, the plug member 100 is elongate along the longitudinal direction L when the plug member 100 is in the insertion configuration, and the first and second ridges 116 and 118 are spaced apart with respect to each other along a lateral direction A that is angularly offset with respect to the longitudinal direction L. Further, the ridges 116 and 118 can project from the body 110 along a transverse direction T that is angularly offset with respect to the lateral and longitudinal directions A and L. The longitudinal direction L can be referred to as a first direction and the lateral direction A can be referred to a second direction, and the transverse direction T may be referred to herein as a third direction. The longitudinal, lateral and transverse directions L, A and T can include first and second directional components that are opposite with respect to each other. For example, the longitudinal direction L can define a first longitudinal direction and a second longitudinal direction that is opposite to the first longitudinal direction. The lateral direction A can define a first lateral direction and a second lateral direction that is opposite to the first lateral direction. The transverse direction T can define a first transverse direction and a second transverse direction that is opposite to the first transverse direction.

Turning to FIGS. 3 and 5, the plug member 100 can define a first or distal end 120 and a second or proximal end 124 spaced from the first end 120 along the longitudinal direction L. The plug member 100 can define a longitudinal or first axis 104 that extends through the first and second ends 120 and 124 and is aligned with the longitudinal direction L. When the plug member 100 is in the insertion configuration the plug member 100 is elongate along a first axis 104 that is aligned with the longitudinal direction L. When the plug member 100 is in the collapsed configuration, the plug member 100 is collapsed along the insertion direction I such that the first axis 104 has a collapsed shape (collapsed axis 104 not shown). The plug member 100 defines a first edge 140 and a second edge 144 spaced apart from the first edge 140 along the lateral direction A. The plug member can define a lateral or second axis 106 aligned with the lateral direction A. The second axis 106 extends through the first and second edges 140 and 144 and intersects the first axis 104. Further, the plug body 110 can further include a first surface 132 and a second surface 136 spaced from the first surface 132 along the transverse direction T. The plug member 100 can also define a transverse or third axis 108 that is aligned with transverse direction T. The third axis 108 extends through the first and second surfaces 132 and 136 and intersects the first and second axes 104 and 106. In accordance with the illustrated embodiment, the first surface 132 is disposed between the first and second ridges 116 and 118.

Referring to FIGS. 3 and 5, the first and second ridges 116 and 118 project from the plug body 110. In accordance with the illustrated embodiment, the first and second of ridges 116 and 118 can project from the plug body 110 along the transverse direction T in a direction T1 away from at least one of the first surface 132. Thus, the first and second ridges 116 and 118 project away from the first surface 132 of the plug body 110 such that the first and second ridges 116 and 118 extend from the plug body 110 in the same general direction. In accordance with alternative embodiments, the first and second ridges 116 and 118 can project from the plug body 110 along the transverse direction T away from at least one of the first surface 132 and the second surface 136. The plug members 400 and 500 shown FIGS. 7A and 7B and discussed below include ridges that project from the plug body 110 along the transverse direction T in respective first and second directions that are not aligned in the same general direction. For instance, the first ridge 116 and can project from the first surface 132 of the plug body 110 in a first direction T1 and the second ridge 118 can project from the second surface 136 of plug body 110 in a second direction T2 that is different than the first direction T1

Turning to FIG. 5, the ridges 116 and 118 are spaced apart along the lateral direction A such that the ridges 116 and 118 and the plug body 110 disposed between the ridges 116 and 118 at least partially define a region 160. The ridges 116 and 118 include respective proximal portions (not numbered) and distal portions 121a and 121b spaced from the proximal portion toward the distal end 120 in the longitudinal direction L. When the plug member 100 is collapsed, the distal portions 121a and 121b of the ridges 116 118 abut the surface of the vessel along opposed transverse ends 5a and 5b of the puncture 4 (see FIG. 9A) while the region 160 disposed between the distal portions 121a and 121b spans the puncture 4. The distal portions 121a and 121b of the ridges 116 and 118 can be aligned with the longitudinal vessel direction VL (not shown) when collapsed against the vessel.

Turning to FIG. 5, the plug member 100 can be sized and configured such that the plug member 100 can partially surround and generally conform to the curvature of the vessel when in the collapsed configuration. In accordance with the illustrated embodiment, the plug body 110 defines a plug length 111 that extends from the first end 120 to the second end 124 along the first axis 104. The plug body 110 defines a first thickness dimension 112 that extends from the first surface 132 to the second surface 136 along the second axis 108. The first and second ridges 116 and 118 each define respective second thickness dimensions 113a and 113b that extend from the first surface 132 of the plug body 110 to respective terminal ends 126 and 128 of the first and second ridges 116 and 118 along the third or transverse axis 108. In accordance with the illustrated embodiment, each second thickness dimension 113a and 113b is each at least twice the first dimension 112. Further, the plug body 110 defines a plug width 114 that extends from the first edge 140 to the second edge 144 along the second axis 106. The first ridge 116 includes opposite sides 117a and 117b and the second ridge 118 includes opposed sides 119a and 119b. The first ridge 116 defines a first ridge width 115a that extends along the second axis 106 from the side 117a to the side 117b. The second ridge 118 defines a second ridge width 115b that extends along the second axis 106 from the side 119a to the side 119b. The combined first and second widths 115a and 115b are no greater than 25% of the plug width 114.

As shown in FIGS. 3 and 5, the first and second ridges 116 and 118 can disposed along at least a portion of a respective one of the first and second edges 140 and 144. In accordance with the illustrated embodiment, the first and second ridges 116 and 118 are aligned or coextensive with the respective edges 140 and 144. However it should be appreciated that the ridge 116 and 118 can be spaced inwardly with respect to each other and away from the respective edges 140 and 144 as needed. Further, the first and second ridges 116 and 118 can extend along at least a portion of plug body 110 in the longitudinal direction L along the respective edges 140 and 144. For instance, the each ridge 116 and 118 extend along respective edges 140 and 140 from the first end 120 to the second along an entirety of the length 111 of the plug member 100. In another embodiment, ridges 116 and 118 extend along a portion of the length 111 of the plug member 100, for example, as illustrated in FIGS. 6A and 6B and discussed next.

Figure 6A:
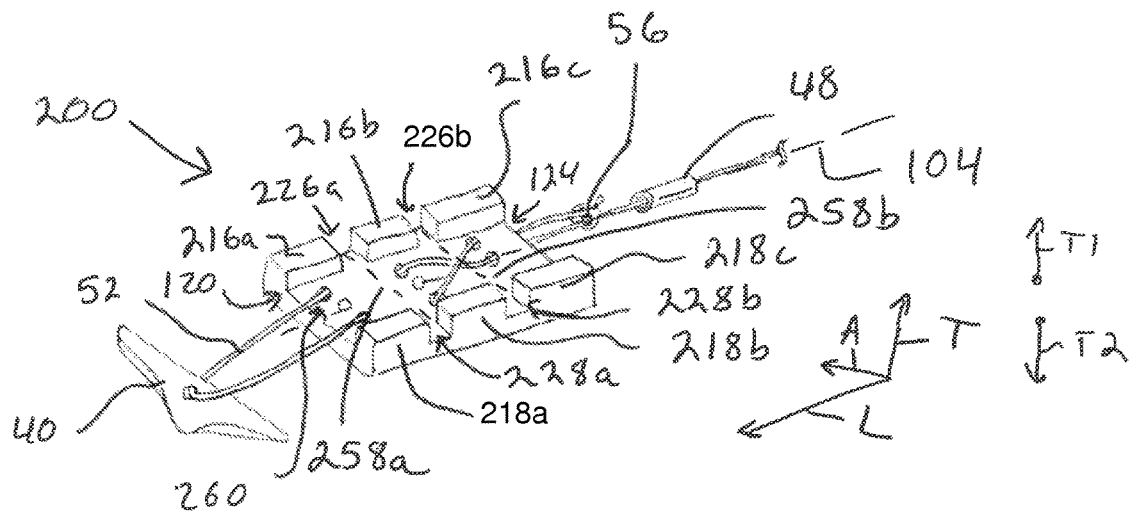
FIG. 6A is a perspective view of a portion of the sealing device shown in FIG. 1, showing the plug member according to another embodiment of the present disclosure.

Turning to FIG. 6A, a plug member 200 according to an alternative embodiment can be attached to the suture 52 proximal to the toggle 40 and distal to locking member as discussed above with respect to embodiments shown FIG. 3. The plug member 200 can be constructed similarly the plug member 100 and similar reference numbers will be used to refer to common elements between plug member 100 and plug member 200. Thus, the plug member 200 can be elongate along the first axis 104 that is aligned with the longitudinal direction L and include a first or distal end 120 and a second or proximal end 124 spaced from the first end 120 along the longitudinal direction L. The first axis 104 can extend through the first and second ends 120 and 124. Although not shown, the plug member 200 can include first and second edges 140 and 144, opposed surfaces 132 and 136 similar to the plug member 100 described above. In accordance with the illustrated embodiment, the plug member 200 includes a plug body 210 and a plurality of first ridges 216a, 216b, and 216c and a plurality of second ridges 218a, 218b, and 218c. Each of the first ridges 216a-216c and second ridges 218a-218c extend along a portion of the length 111 (length 111 not shown in FIG. 6A). The first ridges 216a, 216b, and 216c are separated by a first set of grooves 226a and 226b. The first set of grooves includes a distal groove 226a and a proximal groove 226b. Likewise, the second ridges 218a, 218b, and 218c are separated by a second set of grooves 228a and 228b. The second set of grooves includes a distal grove 228a and a proximal groove 228b. The first set grooves 226a and 226b can be aligned with corresponding second set grooves 228a and 228b along the lateral direction A. In an exemplary embodiment, the distal grooves 226a and 228a can extend along and be aligned with each other along a first fold axis 258a and the proximal grooves 218b and 228b can extend along and be aligned with each other along a second fold axis 258b. Presence of the grooves along the respective fold axes 258a and 258b can facilitate collapse of the plug member about the fold axes 258a and 258b. When the plug member 200 is collapsed against the puncture, the ridges 216a and 218a can abut the surface of the vessel along opposed transverse ends of the puncture while a region 260 disposed between the ridges 216a and 218a spans the puncture 4. It should be appreciated that while the first ridges 216a-216c and the second ridges 218a-218c project from the plug body 210 along the transverse direction T in a first transverse direction T1 as illustrated, the first or second ridges can project from the plug body 210 along a second transverse direction T2 that is different than, for instance opposite to, the first transverse direction T1. The first and second transverse direction T1 and T1 can be angularly offset with respect to the longitudinal direction L. While three first ridges 216a, 216b, and 216c and three second ridges 218a, 218b, and 218c are illustrated, the plug member 200 can include more, for instance greater than two, of the first ridges and the second ridges. Alternatively, the plug member 200 can include two of the first ridges and two of the second ridges. Furthermore, the plug body 210, the first ridges 216a, 216b, and 216c, and the second ridges 218a, 218b, and 218c, can be constructed to have similar dimension as described above with respect to plug member 100 and first and second ridges 116 and 118.

Figure 6B:
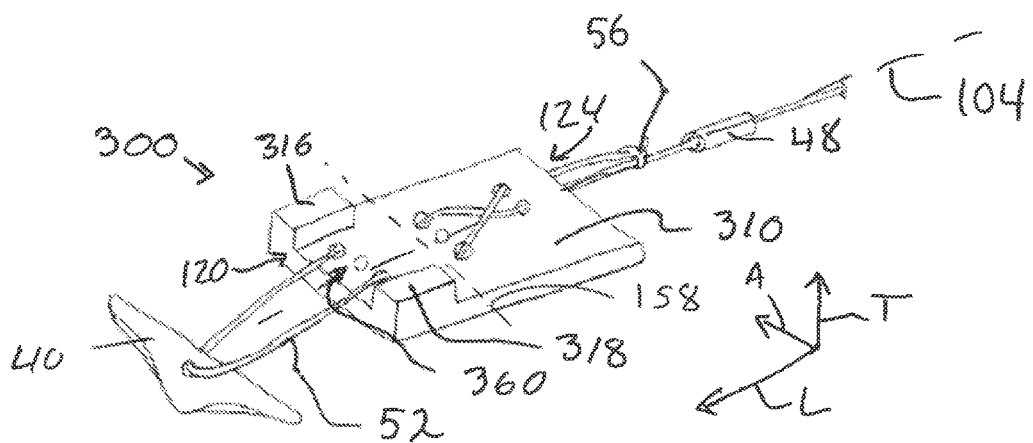
FIG. 6B is a perspective view of a portion of the sealing device shown in FIG. 1, showing a plug member according to another embodiment of the present disclosure.

Turning to FIG. 6B, a plug member 300 according to an alternative embodiment can be attached to the suture 52 proximal to the toggle 40 and distal to the locking member 48 as discussed above with respect to embodiment shown FIG. 3. The plug member 300 can be constructed similarly the plug member 100 and similar reference numbers will be used in FIG. 6A to refer to common elements between plug member 100 and plug member 300. In accordance with the illustrated embodiment, the plug member 200 includes a plug body 310, a first ridge 316 and a second ridge 318 extend along a portion of the length 111 (length 111 not shown in FIG. 6A). The first and second ridges 316 and 318 are disposed toward the distal end 120 of the plug member 300. In accordance with the illustrate embodiment, the first and second ridges are disposed distal to the fold axis 158a. Although the ridges 316 and 318 can extend across the fold axis 158a as needed. In the exemplary embodiment shown, the first and second ridges 316 and 318 define a ridge length (not labeled) that extends along the longitudinal L that is less than half the length 111 of the plug member 300. Further, the ridges 316 and 318 are spaced apart along the lateral direction A, such that the ridges 316 and 318 and the plug body 310 disposed between the ridges 316 and 318 at least partially define a region 360. The ridges 316 and 318 project from the plug body 310 such that when the plug member 300 is collapsed, the first and second ridges 316 and 318 abut the surface of the vessel along opposed transverse ends of the puncture while the region 360 disposed between the ridges 316 and 318 spans the puncture 4. Further, the ridges 316 and 318 can be aligned with the longitudinal vessel direction VL (not shown) when collapsed against the vessel.

Figure 7A:
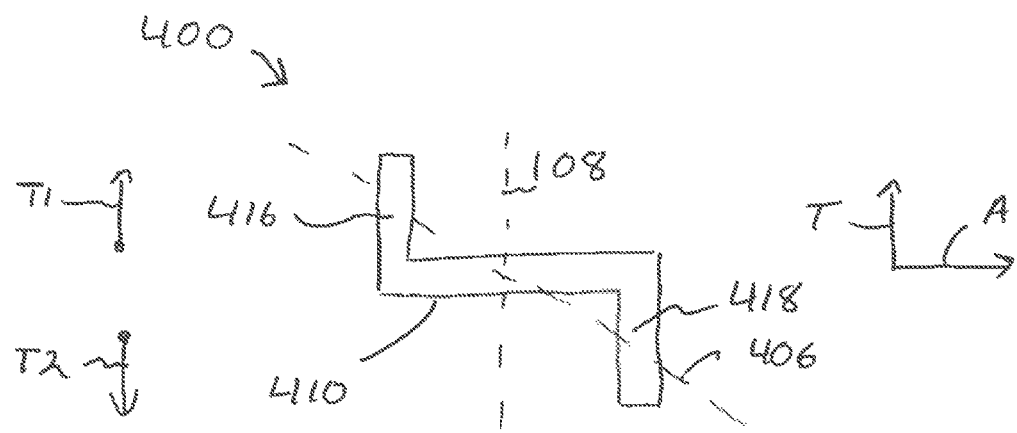
FIG. 7A is an end view of a plug member according to another embodiment of the present disclosure.
Figure 7B:
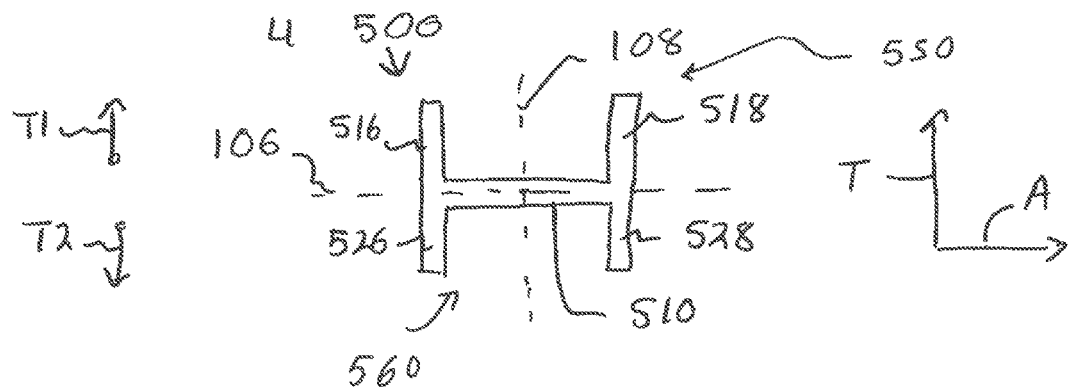
FIG. 7B is an end view of a plug member according to another embodiment of the present disclosure.

Turning to FIGS. 7A and 7B, alternative plug members 400 and 500 are illustrated that are configured collapsed against the vessel and cover the puncture as described above with respect to plug member 100, 200 and 300. Plug members 400 and 500 can be attached to the suture 52 proximal to the toggle 40 and distal to the locking member 48 as discussed above with respect to plug member 100 shown FIG. 3. Further, each plug member 400 and 500 can be constructed similarly the plug member 100 and similar reference numbers will be used in FIGS. 7A and 7B to refer to common elements between plug member 100 and plug member 400 and 500.

Referring to FIG. 7A, the plug member 400 includes plug body 410, first ridge 416 and second ridge 418 that project from the plug body 410 along transverse direction T that is aligned with the transverse axis 108. The first ridge 416 can project from the plug body in a first transverse direction T1 and the second ridge can project from the plug body 410 in the second transverse direction T2 that is different from the first transverse direction T2. Further, the first and second ridges 316 and 318 can be spaced apart with respect to each along the lateral direction A or an axis 406 that is angularly offset with respect to the first axis 104 (not shown) and transverse axis 108. As shown in FIG. 7B, the plug member 500 can include a plug body 510, a first pair of ridges 550 that project from the plug body 510 in a first transverse direction T1, and a second pair of ridges 560 that project from the plug body 510 along the second direction T2. The first pair of ridges 550 includes a first and second ridge 516 and 518. The second pair of ridges 560 includes first and second ridges 526 and 528. It should be appreciated that each respect ridges 516, 518, 526, and 528 can project along a respective direction away from the plug body 510. For instance, the first and second ridges 516 and 518 of the first pair of ridges 550 can be extend along parallel directions as illustrated, or the first and second ridges can be angularly offset with respect to each other. Furthermore, the first and second ridges 526 and 528 of the second pair of ridges 560 can be extend along parallel directions as illustrated, or the first and second ridges 526 and 528 can be angularly offset with respect to each other.

As shown in FIGS. 1, 3 and 5, the plug member 100 can have a plurality of suture receiving apertures 76 that receive the suture 52 along the proximal and distal directions 7 and 9 to thereby couple the plug member 100 to the suture 52. Each of the suture receiving apertures 76 are disposed between the opposed first and second edges 140 and 144 of the plug member body 110. At least one of the apertures can be aligned along the first axis 104. For instance, an aperture 77 can be aligned along the first axis 104. The plug member 100 can further include a series of guide wire apertures 80 that receive the guide wire 72 during insertion of the closure device 18 into the vessel. Further plug member 100 can include a select location 148 aligned with one of the apertures 76. In accordance with the illustrated embodiment, the select location 148 is aligned the aperture 77 such that the select location 148 is aligned with the first axis 104. The location of the apertures 77 direct a force to the select location 148 of the plug body 110 as the plug member 100 is being collapsed against the puncture 4, as will be further detailed below.

The plug member 100 can comprise a strip of compressible, resorbable, collagen foam and can be made of a fibrous collagen mix of insoluble and soluble collagen that is cross linked for strength. It should be appreciated, however, that the plug member 100 can have any configuration as desired and can be made from any material as desired.

With continued reference to FIG. 1, the locking member 48 is configured to frictionally engage the suture 52 as the locking member 48 is moved along the suture 52 toward the toggle 40 to thereby seal the puncture. That is, the locking member 48 is configured to remain in place on the suture 52 when no force is placed on the locking member 48, and only overcomes its frictional engagement with the suture 52 in response to an application of force on the locking member 48. Application of the force to the locking member 48 urges the locking member 48 in contact with the select location 148 of the plug body 110. When the locking member 48 engages the select location 148, forces are distributed along the plug member 100 along a direction transverse to the direction that the force is applied to the select location 148. Because the select location 148 is disposed between the opposed edges 140 and 144 of the plug body 110, application of the force via the locking member 48 against the plug body 110 urges the ridges 116 and 118 against the surface of the vessel that curves away from puncture 4, such that the plug member 100 generally conforms to the curvature of the vessel. The locking member 48 can be configured as a cylindrical member that is crimped onto the suture 52. It should be appreciated, however, that the locking member 48 can have other configurations as desired. For example, the locking member 48 can be the slideable knot 56. In such an embodiment, the slidable knot 56 can be a locking knot.

As shown in FIG. 1, the closure device 18 further includes a tamper 90 proximal to the locking member 48 and a tensioning device 92 proximal to the tamper 90. As shown, the guide wire 72 and the suture 52 extend through both the tamper 90 and the tensioning device 92. The tamper 90 is configured to be translated along the suture 52 to thereby move the locking member 48 against the plug member 100 toward the select location 148. In this way, the tamper 90 can transition the plug member 100 from the insertion configuration in the collapsed configuration, and or further compress the plug member 100 when the plug member is in a collapsed configuration but not fully seated against the vessel wall. In this way, the tamper 90 can help fully seal the puncture. The tensioning device 92 is configured to maintain the suture 52 in tension during the sealing procedure.

FIGS. 8A through 10B illustrate transition of the plug member 100 from the initial configuration as shown FIGS. 8A and 8B, whereby the plug member is elongate along the suture 52, into an intermediate configuration shown in FIGS. 9A and 9B, when the plug member 100 is collapsed along the insertion direction I yet the plug member 100 is not fully seated or compressed against the vessel, and further into the collapsed configuration shown FIGS. 10A and 10B, whereby the locking member 48 is compressed against the collapsed plug member 100, locking the plug member 100 against the puncture 4. Turning to FIGS. 8A and 8B, when the toggle 40 is inserted in the vessel 1 and positioned against an inner surface of the vessel wall 2 adjacent to the puncture 4, the distal end 120 of the plug member 100 is disposed above the vessel wall 2 opposite the toggle 40. In accordance with the illustrated embodiment, the first and second ridges 116 and 118 project from plug body 110 along the transverse direction T. The ridges 116 and 118 are spaced apart with respect to each other along the lateral direction A so as to be positioned adjacent to or disposed outwardly from the opposed transverse ends 5a and 5b of the puncture 4.

As shown in FIGS. 9A and 9B, at least one of a tension applied to the suture 52 and a force applied to the select location 148 of the plug body 110 causes the plug member 100 to collapse along the insertion direction I such that the distal portions 121a and 121b ridges 116 and 118 are in contact with the vessel wall 2 and the region 160 of the plug body 110 between the distal portions 121a and 121b of the ridges 116 and 118 span the puncture 4 along the transverse direction VT of the vessel. The distal portions 121a and 121b of the ridges 116 and 118 are also aligned along the longitudinal direction of the vessel VL such that puncture 4 extends along vessel transverse direction VT between the location where the first and second ridges 116 and 118 contact the vessel wall 2.

Turning to FIGS. 10A and 10B, application of a force F to the locking member 48 causes the locking member 48 to move into engagement the with the select location 148 of the plug member 100, which compresses the plug member 100 against the vessel wall 2. Because the ridges 116 and 118 project from the plug body 110 toward the and away from the puncture 4, and plug body region 160 spans the puncture 4, compression of the plug member 100 at the select location 148 causes the plug member 100 to conform to the curvature of the vessel 1. Thus, when the plug member 100 is collapsed against the puncture, a portion of the ridges 116 and 118 and a portion of the plug member body 110 define a vessel-engaging portion 152 the shape of the vessel wall 2. The vessel-engaging portion 152 can include a curved surface that conforms to the curvature of the vessel.

Embodiments of the present technology will now be described with respect to exemplary large bore procedures that utilize the puncture sealing device 10. In order to perform any of the related procedures, the user gains percutaneous access to, for example, the femoral artery, causing a puncture in the artery. To gain percutaneous access to the artery, the Seldinger technique may be used. For example, a hollow bore needle is inserted into the artery. The guide wire 72 is then advanced through the hollow needle and into the femoral artery a sufficient distance to allow removal of the needle without the guide wire 72 pulling out of the vessel. Removing the needle leaves the guide wire 72 in place, with a portion of the guide wire 72 extending into the artery. The guide wire 72, extending from outside the patient into the femoral artery, provides for an entry guide for other medical devices including the puncture sealing device 10. Therefore, once the guide wire 72 is positioned in the vessel of the patient, catheters, or introducers, or gradually increasing diameters are advanced over the guidewire and through the puncture into the artery to further open the puncture. Then, an introducer/procedure access sheath set (i.e. an introducer inside an access tube or sheath) is moved along the guide wire 72 such that a distal end of the sheath moves into the vessel through the puncture. And once positioned, the introducer can be removed such that the sheath provides for sizable access to the vessel interior from outside the body.

After the relevant procedure is completed, the puncture in the artery created by the bore needle during percutaneous access of the artery may be closed. The puncture sealing device 10 as described above may be used to seal the puncture 4. FIGS. 11A-11I show schematic views of the puncture-sealing device 10 during the process of closing a puncture 4 in a vessel wall 2.

Figure 11A:
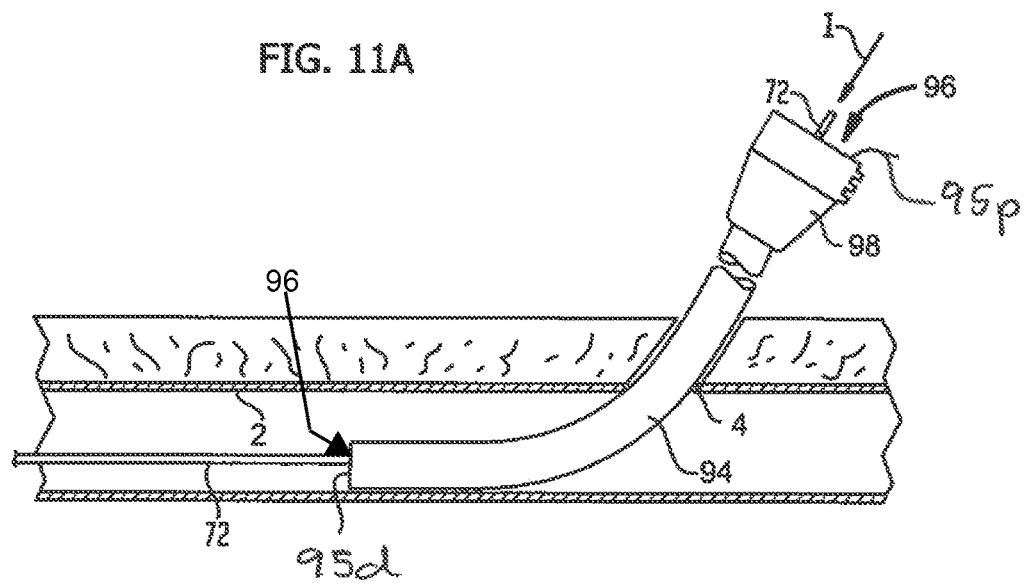
FIG. 11A is a schematic showing an access sheath partially disposed within the vessel through the puncture in the vessel.

Now in reference to FIG. 11A, to deliver the puncture sealing device 10 to the puncture 4 so that the closure device 18 can seal the puncture 4, the introducer/procedure sheath set is replaced with a closure access sheath 94. For example, as shown in FIG. 11A, the procedure sheath is exchanged for the closure access sheath 94 by removing the procedure sheath from the patient, leaving the guide wire 72 in place, and subsequently moving the closure access sheath 94 along the guide wire 72 or otherwise positioning the access sheath 94, such that a portion of the access sheath 94 is disposed within the vessel through the puncture 4. As shown in FIG. 11A, the access sheath 94 defines a distal end 95d, a proximal end 95p, and an access channel 96 that extends from the proximal end 95p to the distal end 95d along an insertion direction I. The insertion direction I can be aligned with the longitudinal direction L. The access sheath 94 further includes a sheath hub 98 at its proximal end 95p. The sheath hub 98 is configured to couple to the puncture sealing device 10 when the puncture sealing device 10 is inserted into the access channel 96 along the insertion direction I.

Figure 11B:
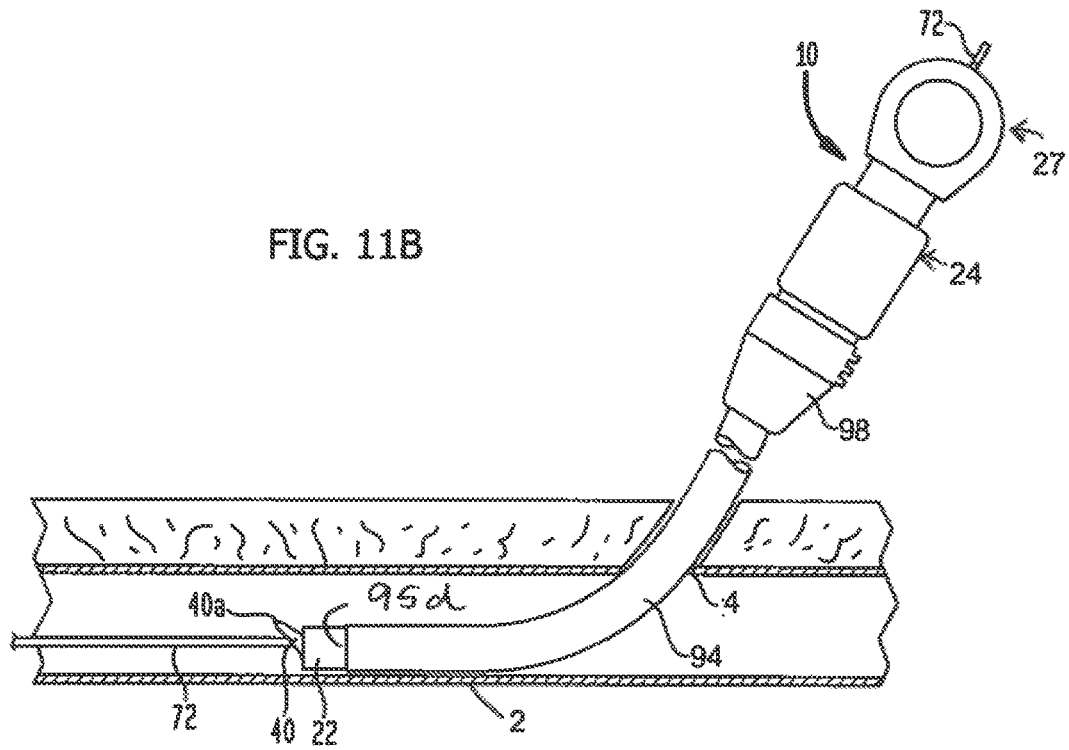
FIG. 11B is a schematic showing the closure device of FIG. 1 translated into an access channel of the access sheath such that a distal end of the toggle is positioned distal to a distal end of the access sheath.

As shown in FIG. 11B, the puncture sealing device 10 can be positioned by translating the puncture sealing device 10 into the access channel 96 (not shown) along the insertion direction I such that at least the distal end 40a of the toggle 40 protrudes from the distal end D of the access sheath 94 and into the vessel. Once fully inserted, the puncture-sealing device 10 can couple to the sheath hub 98. As shown in FIG. 11B, the proximal end 40b of the toggle 40 is trapped within the retention cavity 32 between the release tube 22 and the delivery tube 30 while the puncture sealing device 10 is being moved into the vessel through the puncture 4 of the vessel. While the proximal end 40b of the toggle 40 is trapped, the toggle 40 is oriented in a pre-sealing position whereby at least the proximal end 40b of the toggle 40 is prevented from dragging against the vessel wall during positioning of the toggle 40 within the vessel.

Figure 11C:
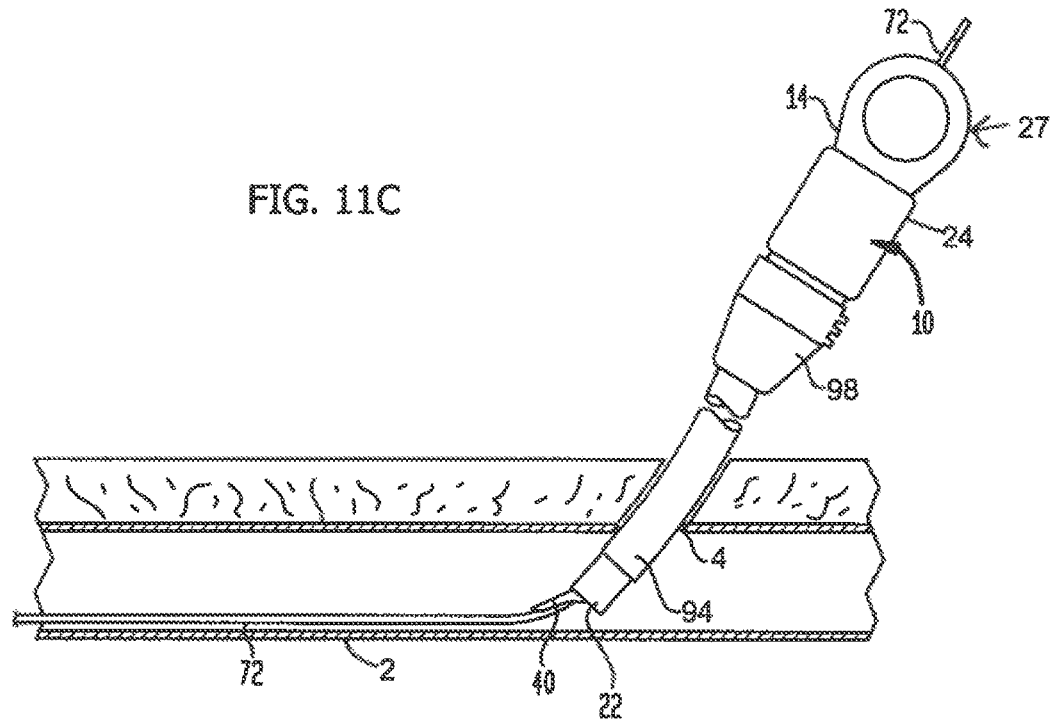
FIG. 11C is a schematic showing the access sheath and closure device combination pulled proximally such that the toggle is proximate to the puncture.
Figure 11D:
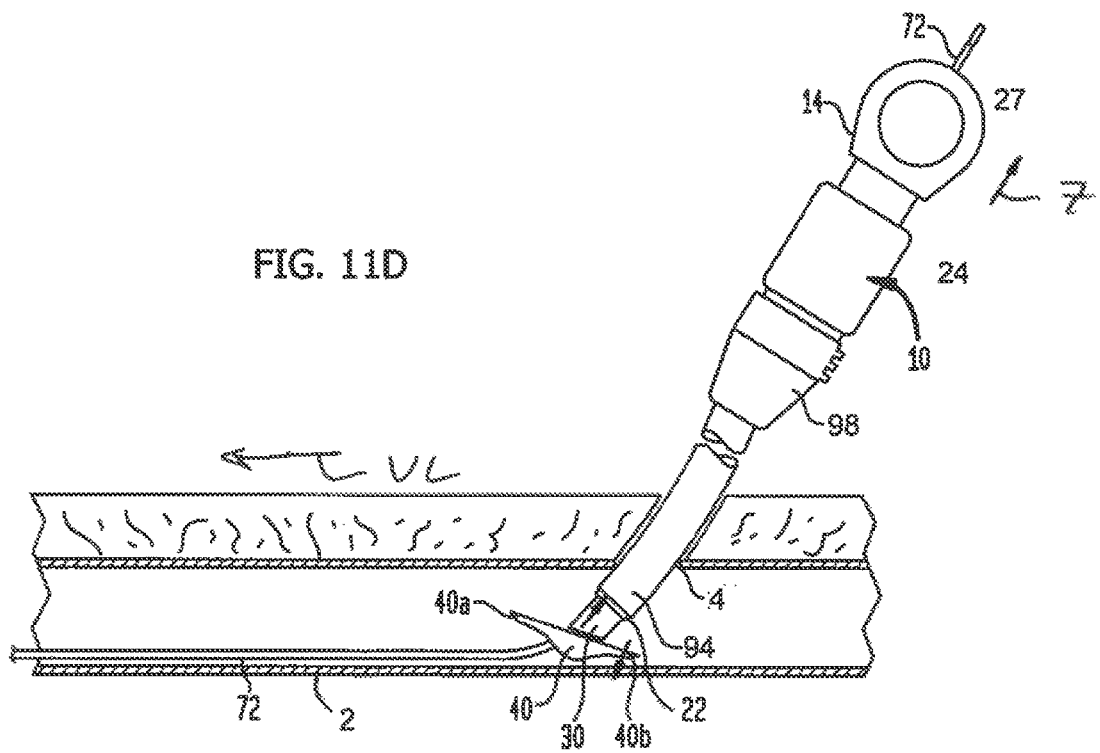
FIG. 11D is a schematic showing the release tube being moved proximally relative to the delivery tube to thereby release the toggle.

Once the puncture sealing device 10 is properly positioned within the access sheath 94, the toggle 40, and in particular, the entire access sheath 94 and puncture-sealing device 10 combination can be moved in the proximal direction 7 such that the toggle 40 is adjacent the puncture 4. While the toggle 40 is being positioned adjacent the puncture 4 the toggle 40 is in the pre-sealing position as shown in FIG. 11C. And once the toggle 40 is in position, at least one of the delivery tube 30 and the release tube 22 can be moved relative to the other such that the proximal end 40b of the toggle 40 is released from the release tube 22 or is otherwise removed from the retention cavity 32 defined between the release tube 22 and the delivery tube 30. In the illustrated embodiment, and in reference to FIG. 11D, the actuator 27 can be moved along the proximal direction 7 such that the release tube 22 is moved proximally relative to the delivery tube 30 to thereby release the proximal end 40b of the toggle 40 from the retention cavity 32.

Figure 11E:
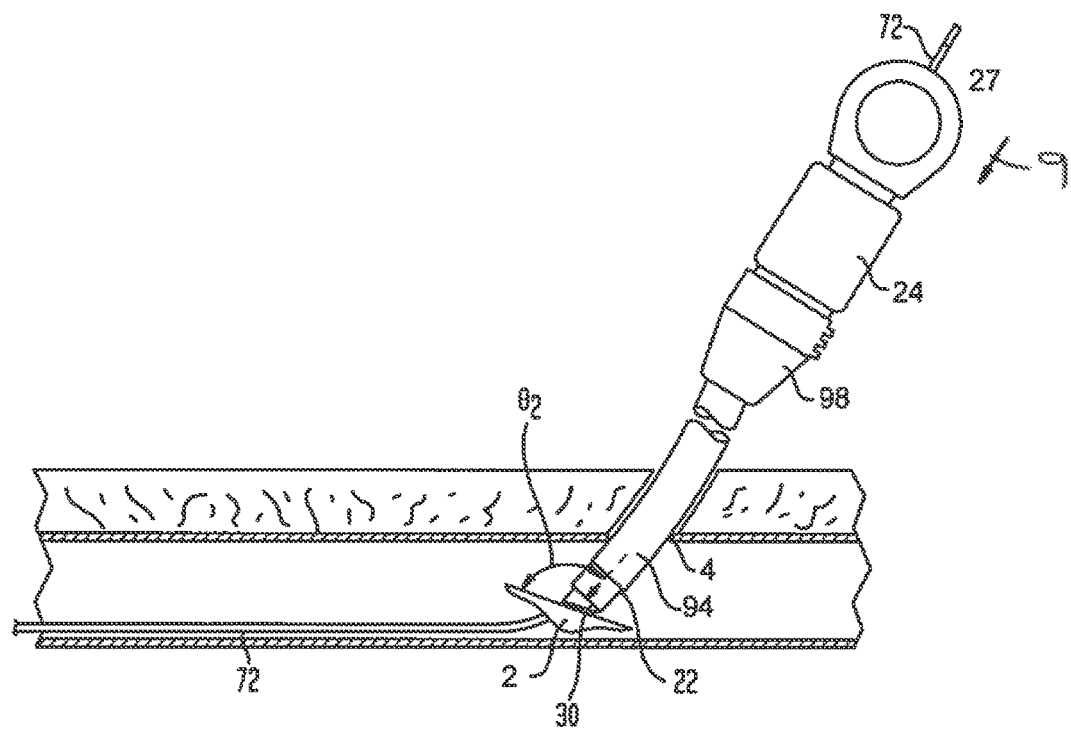
FIG. 11E is a schematic showing the release tube being moved distally relative to the delivery tube such that the release tube abuts the toggle to thereby orient the toggle in a sealing position.

As shown in FIG. 11E, at least one of the delivery tube 30 and the release tube 22 can be moved relative to the other such that a distal end of the release tube 22 abuts the toggle 40 to thereby orient the toggle 40 in a sealing position whereby the toggle is angled by a second angle $Ø_2$ relative to the central axis of the release tube 22 that is different than the first angle $Ø_1$. In particular, the second angle $Ø_2$ is smaller than the first angle $Ø_1$.

In the illustrated embodiment, the release tube 22 is moved distally relative to the delivery tube 30 so that the release tube 22 can abut the toggle 40 and orient it in the sealing position. As shown in FIG. 11E, the toggle 40 is angled relative to the delivery tube 30 when in the sealing position. The angled orientation of the toggle 40 is such that the toggle 40 remains within the vessel when the toggle 40 is pulled against the vessel wall 2.

While the toggle 40 is in the sealing position, a tension can be applied to the suture 52. For example, the suture 52 can be pulled proximally relative to the delivery tube 30 to thereby ensure that the toggle 40 remains in the sealing position whereby the toggle 40 abuts the release tube 22. The tension can be applied to the suture prior to the release tube 22 being moved to abut the toggle 40, after the release tube 22 has been moved to abut the toggle 40, or at the same time the release tube 22 is being moved.

Figure 11F:
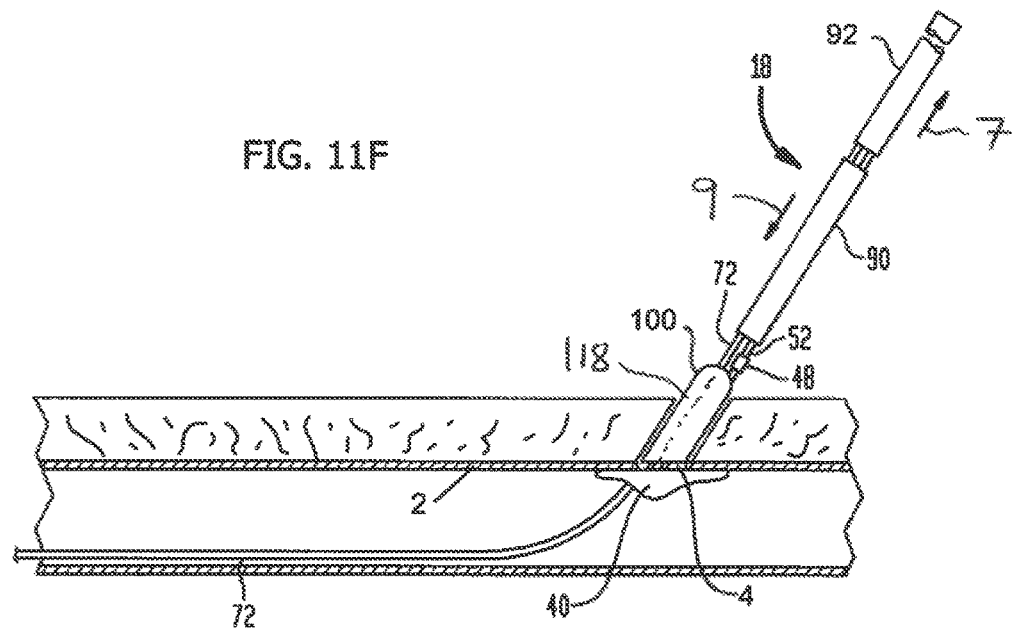
FIG. 11F is a schematic showing the deployment assembly being pulled proximally such that the toggle abuts the vessel wall and a plug that is coupled to the toggle with a suture is deployed from the delivery tube.

With the toggle 40 in the sealing position as shown in FIG. 11E, the deployment assembly 14 along with the access sheath 94 can together be pulled proximally such that the plug member 100 and other components of the closure device 18 emerge from the delivery tube 30. As shown in FIG. 11F, the closure device 18, including the toggle 40, plug member 100, locking member 48, suture 52, tamper 90, and tensioning device 92, are fully withdrawn from the delivery tube 30. By pulling on the tensioning device 92 in the proximal direction 7 away from the vessel (i.e. in a direction opposite the insertion direction I) the suture 52 is tensioned and the toggle 40 is moved fully into position against an inner surface of the vessel wall 2 at the puncture 4. The tension in the suture 52 also pulls the plug member 100 into the puncture 4, and causes the plug member 100 to fill the tissue opening proximate the vessel puncture 4 as shown in FIG. 11F. After the plug member 100 is in contact with blood or other fluids within the puncture 4, the plug member 100 will expand and fill the remainder of the tissue bore.

Figure 11G:
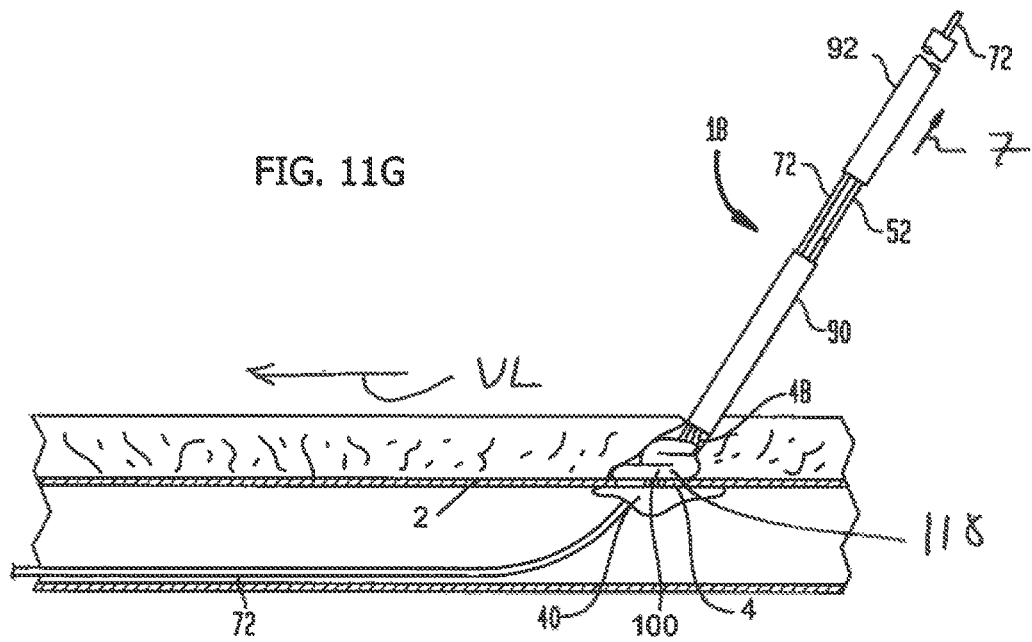
FIG. 11G is a schematic showing the plug being pressed against the vessel wall with a locking member while the guide wire remains in place.

After the user has pulled the tensioning device 92 to cause tension in the suture 52 and to cause the plug member 100 to abut the puncture 4, the user advances the tamper 90 along the guide wire 72 and the suture 52. As shown in FIG. 11G, the tamper 90 contacts the locking member 48 and advances the locking member 48 along the suture 52 until the locking member 48 contacts the selection location 148 of the plug member 100 and presses the plug member 100 against an outer surface of the vessel, thereby collapsing the plug member 100 into the collapsed configuration. In this position, as discussed above a portion of the ridges 116 and 118 (116 not shown) are aligned along the longitudinal vessel direction VL. As the plug member 100 is compressed by the tamper 90 the plug member 100 folds over the top of and inside the puncture 4. It should be appreciated, however, that in some embodiments, the delivery tube 30 is pulled such that the plug member 100 is removed from the delivery tube 30 within the release tube 22 and the tamper 90 is employed within the release tube 22. In such an embodiment, the release tube 22 helps control the plug member 100 as it is being tamped against the puncture.

Figure 11H:
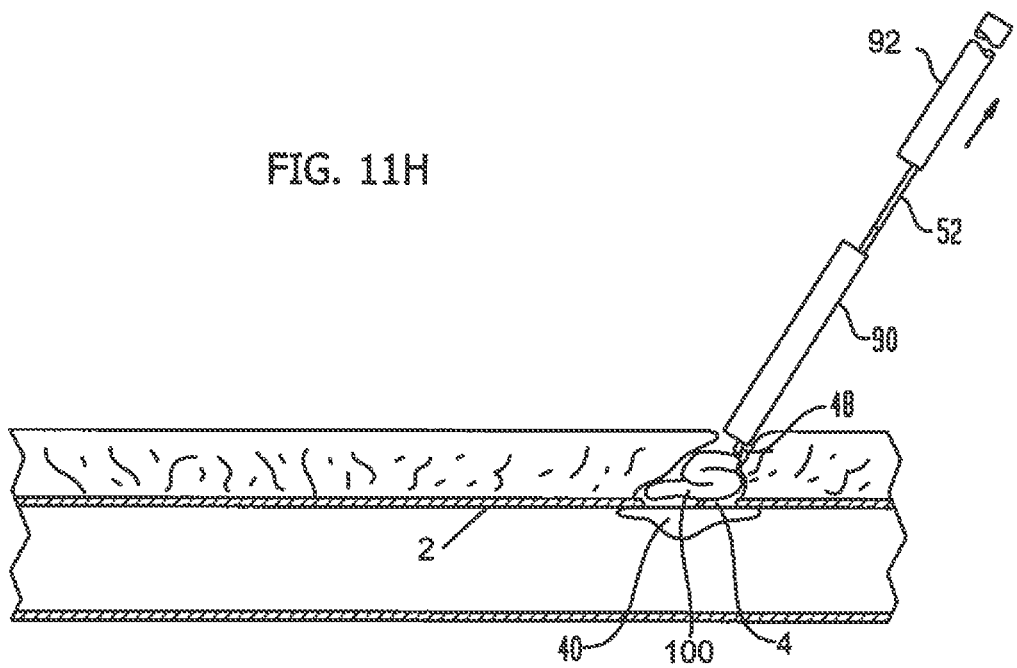
FIG. 11H is a schematic showing the locking member being tamped against the plug with a tamper of the closure device after the guide wire has been removed.
Figure 11I:
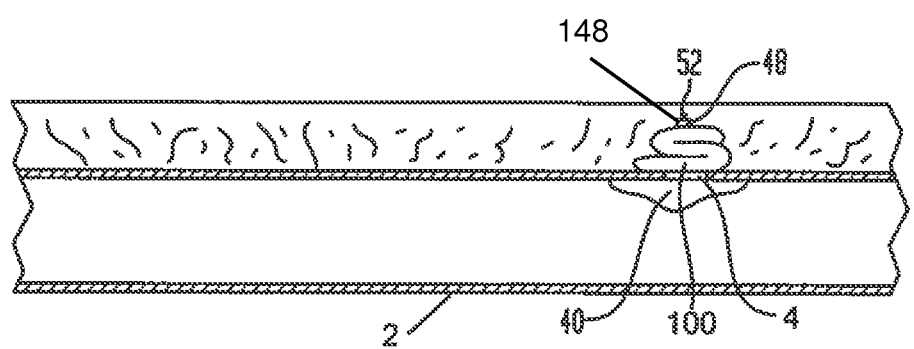
FIG. 11I is a schematic showing the plug member in collapsed configuration covering the puncture.

As shown in FIGS. 11H and 11I, the locking member 48, together with the plug member 100 and the toggle 40 effect a seal of the puncture 4. As shown in FIG. 11H, tension is maintained on the tensioning device 92 throughout the deployment of the plug member 100 from the delivery tube 30. After the puncture 4 is sealed, the guide wire 72 can be removed as shown in FIG. 11H. As the guide wire 72 is removed, the suture 52 remains in tension and the user can re-compress the plug member 100 with the tamper 90 as desired to confirm a proper seal of the puncture 4. Once properly sealed, the suture 52 can be cut below the tamper 90 so that the remaining suture 52, tamper 90, and tensioning device 92 can be removed from the puncture 4, as shown in FIG. 11I. Remaining portions of the closure device 18, including the toggle 40, plug member 100, portion of suture 52, and locking member 48 (depending on material used) will resorb into the body of the patient over time.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A vascular closure device, comprising:
    a delivery assembly configured to be inserted into a puncture of a vessel;
    an anchor member carried by the delivery assembly;
    a suture attached to the anchor member and extending into the delivery assembly; and
    a plug member disposed in the delivery assembly, the plug member attached to the suture so that the plug member is proximal to the anchor member, the plug member including a plug body that is elongate along a central longitudinal axis of the plug member when the plug member is in an insertion configuration, and
    a pair of ridges that:
        a) project from the plug body and on either side of the longitudinal axis, and
        b) are elongate along the longitudinal axis when the plug member is in an insertion configuration,
    the plug body further including a select location comprising a plurality of proximal apertures and a plurality of distal apertures that are disposed between the pair of ridges,
    the plurality of proximal apertures including a first aperture disposed along the central longitudinal axis and a second aperture offset from the central longitudinal axis, the plurality of distal apertures including at least one aperture offset from the central longitudinal axis,
    wherein the suture is attached to the plug member through the plurality of proximal apertures and the plurality of distal apertures,
    wherein the plug member is configured to, in response to a force applied to the select location, transition from the insertion configuration, whereby the plug member is elongate along the insertion direction, into a collapsed configuration, whereby the plug member is collapsed along the insertion direction,
    wherein when the plug member is deployed against the puncture in the collapsed configuration, a portion of the plug body and a portion of the pair of ridges cover the puncture and conforms to a shape of the vessel adjacent the puncture.

2. The vascular closure device of claim 1, further comprising a lock member attached to the suture and configured to abut the plug member, wherein the lock member is configured to apply the force against the plug member, thereby causing the plug member to conform to the shape of the vessel.

3. The vascular closure device of claim 1, wherein when the plug member is in the insertion configuration, 1) the plug body is elongate along a first direction that is aligned with insertion direction, and 2) the at least one pair of ridges are spaced apart with respect to each other along second direction that is angularly offset with respect to the first direction.

4. The vascular closure device of claim 3, where each ridge of the pair of ridges project from the plug body along a third direction that is angularly offset with respect to the first and second directions.

5. The vascular closure device of claim 3, wherein the pair of ridges include a first ridge and a second ridge, and each ridge projects from the plug body in different directions.

6. The vascular closure device of claim 3, wherein the pair of ridges is a first pair of ridges, and the second direction is a transverse direction, wherein the plug member includes a second pair of ridges, and at least one of the first pair of ridges and the second pair of ridges project from the plug body in a first transverse direction aligned with the transverse direction, and the other of the at least one first and second pairs of ridges project from the body in a second transverse direction that is different than the first transverse direction.

7. The vascular closure device of claim 1, wherein the plug body defines a first edge and a second edge opposite the first edge, and each ridge is disposed along at least a portion of a respective one of the first and second edges.

8. The vascular closure device of claim 7, wherein each ridge of the pair of ridges include at least one groove.

9. The vascular closure device of claim 1, wherein the plug body defines a first thickness and the pair of ridges define a second thickness that is greater than the first thickness when the plug member is in the insertion configuration.

* * * * *